US009273360B2

(12) United States Patent
Jay et al.

(10) Patent No.: US 9,273,360 B2
(45) Date of Patent: Mar. 1, 2016

(54) **DETECTION OF METHICILLIN-RESISTANT *STAPHYLOCOCCUS AUREUS***

(71) Applicant: bioMerieux S. A., Marcy-l'Etoile (FR)

(72) Inventors: Corinne Jay, Seyssins (FR); Birgit Deiman, Olsterwijk (NL); Dianne Van Strijp, 's-Hertogenbosch (NL); Paul Van de Wiel, Eindhoven (NL)

(73) Assignee: bioMerieux S. A., Marcy-l'Etoile (FR)

( * ) Notice: Subject to any disclaimer, the term of this patent is extended or adjusted under 35 U.S.C. 154(b) by 34 days.

(21) Appl. No.: 13/729,529

(22) Filed: Dec. 28, 2012

(65) Prior Publication Data

US 2013/0203056 A1  Aug. 8, 2013

Related U.S. Application Data

(63) Continuation of application No. 12/339,471, filed on Dec. 19, 2008, now Pat. No. 8,367,337.

(60) Provisional application No. 61/008,680, filed on Dec. 21, 2007.

(51) Int. Cl.
  *C12Q 1/68* (2006.01)
  *C12P 19/34* (2006.01)
  *C07H 21/04* (2006.01)

(52) U.S. Cl.
  CPC .......... *C12Q 1/689* (2013.01); *C12Q 2600/106* (2013.01); *C12Q 2600/16* (2013.01)

(58) Field of Classification Search
  USPC ...................... 435/91.2, 810, 6.12; 536/24.33
  See application file for complete search history.

(56) References Cited

U.S. PATENT DOCUMENTS

| | | | |
|---|---|---|---|
| 5,702,895 | A | 12/1997 | Matsunaga et al. |
| 6,156,507 | A | 12/2000 | Hiramatsu et al. |
| 6,379,897 | B1 | 4/2002 | Weidenhammer et al. |
| 7,449,289 | B2 | 11/2008 | Huletsky et al. |
| 7,888,075 | B2 | 2/2011 | McCarthy et al. |
| 8,367,337 | B2 | 2/2013 | Jay et al. |
| 2004/0076990 | A1 | 4/2004 | Picard et al. |
| 2005/0019893 | A1 | 1/2005 | Huletsky et al. |
| 2006/0057613 | A1 | 3/2006 | Ramakrishnan et al. |
| 2007/0054296 | A1 | 3/2007 | Piepenburg et al. |
| 2007/0082340 | A1 | 4/2007 | Huletsky et al. |
| 2008/0227087 | A1 | 9/2008 | Huletsky et al. |
| 2009/0035780 | A1* | 2/2009 | McCarthy et al. ................ 435/6 |
| 2009/0081663 | A1 | 3/2009 | Paitan |

FOREIGN PATENT DOCUMENTS

| | | |
|---|---|---|
| EP | 0887424 A2 | 12/1998 |
| EP | 1 529 847 B1 | 4/2006 |
| EP | 1903116 A1 | 3/2008 |
| JP | 2000-316574 A | 11/2000 |
| JP | 2004-534537 A | 11/2004 |
| JP | 2006-271370 A | 10/2006 |
| WO | WO 97/31125 A2 | 8/1997 |
| WO | WO 02/099034 A2 | 12/2002 |
| WO | WO 2006/111028 A1 | 10/2006 |
| WO | WO 2007/044873 A2 | 4/2007 |
| WO | WO 2008/080620 | 7/2008 |
| WO | WO 2008/129428 A2 | 10/2008 |
| WO | WO 2009/018000 A1 | 2/2009 |
| WO | WO 2009/090310 A1 | 7/2009 |

OTHER PUBLICATIONS

BD GeneOhm™ MSRA Test—Schnellnachweis von Methicillin-resistenten *Staphylococcus aureus*.
BD GeneOhm™ MRSA Test Brochure (2006).
Deurenberg et al., "Directe en snelle detectie van meticillineresistente *Staphylococcus aureus* (MRSA)," Nederlands Tijdschrift voor Medische Microbiologie 15:97-1003 (Sep. 2007).
Dorak "Real-time PCR, Advanced Methods," Taylor & Francis Group, p. 97 (2006).
Elsayed et al., "Development and validation of a molecular beacon probe-based real-time polymerase chain reaction assay for rapid detection of methicillin resistance in *Staphylococcus aureus*," Arch. Pathol. Lab. Med. 127:845-849 (2003).
E-mail from Andrea Rosales evidencing publication date of Podzorski et al. (2007).
German translation of Deurenberg et al., "Directe en snelle detectie van meticillineresistente *Staphylococcus aureus* (MSRA)," Nederlands Tijdschrift voor Medische Microbiologie 15:97-1003 (Sep. 2007).
Herdewijn, "Oligonucleotide Synthesis—Methods and Applications," Humana Press, p. 276 (2005).
Hiramatsu et al., "The emergence and evolution of methicillin-resistant *Staphylococcus aureus*," Trends Microbiol. 9:486-493 (2001).
Hougardy et al., "Direct and fast detection of methicilin resistant *Staphylococcus aureus* carriage by automated nucleic acid extraction and real time PCR," Pathol. Biol. 54:477-481 (2006).
Ito et al., "Structural comparison of three types of staphylococcal cassette chromosome *mec* integrated in the chromosome of methicillin-resistant *Staphylococcus aureus*," Antimicrob. Agents Chemother. 45:1323-1336 (2001).
Jansohn, "Gentechnische methoden: Eine sammlung von arbeitsanleitungen für das molekularbiologische labor," pp. 153-157 (2007).
Martineau et al., "Correlation between the resistance genotype determined by multiplex PCT assays and the antibiotic susceptibility patterns of *Staphylococcus aureus* and *Staphylococcus epidermis*," Antimicrob. Agents Chemother. 44:231-238 (2000).
McPherson et al., "PCR," Second Edition, Taylor & Francis, p. 218 (2006).

(Continued)

*Primary Examiner* — Kenneth R. Horlick
*Assistant Examiner* — Joyce Tung
(74) *Attorney, Agent, or Firm* — Myers Bigel & Sibley, P.A.

(57) ABSTRACT

The present invention provides improved tests for the detection of methicillin-resistant *Staphylococcus aureus*. The tests are particularly useful for eliminating false positive results due to the presence of a mixed bacterial population in patient samples.

20 Claims, 2 Drawing Sheets

(56) References Cited

OTHER PUBLICATIONS

Oberdorfer et al., "Evaluation of a single-locus real-time polymerase chain reaction as a screening test for specific detection of methicillin-resistant *Staphylococcus aureus* in ICU patients," Eur. J. Clin. Microbiol. Infect. Dis. 25:657-7663 (2006).
Oliveira et al., "The evolution of pandemic clones of methicillin-resistant *Staphylococcus aureus*: Identification of two ancestral genetic backgrounds and the associated *mec* elements," Microb. Drug Resistance 7:349-361 (2001).
Oliveira et al., "Multiplex PCR strategy for rapid identification of structural types and vairants of the *mec* element in methicillin-resistant *Staphylococcus aureus*," Antimicrob. Agents Chemother. 46:2155-2161 (2002).
Paule et al., "Performance of the BD GeneOhm methicillin-resistant *Staphylococcus aureus* test before and during high-volume clinical use," J. Clin. Microbiol. 45:2993-2998 (Jul. 2007).
Podzorski et al., "Evaluation of the MVPlex assay for direct and rapid detection of methicillin-resistant *Staphylococcus aureus* from nares and other swab specimens," Abstract C-237, Am. Soc. Microbiol. 107$^{th}$ General Meeting, (May 2007).
Podzorski et al., "MVPlex assay for direct detection of methicillin-resistant *Staphylococcus aureus* in naris and other swab specimens," J. Clin. Microbiol. 46:3107-3109 (Sep. 2008).
Reischl, et al., "Rapid identification of methicillin-resistant *Staphylococcus aureus* and simultaneous species confirmation using real-time fluorescence PCR," J. Clin. Microbiol. 38:2429-2433 (2000).
Stamper et al., "'Clinical validation of the molecular BD GeneOhm StaphSR assay for direct detection of *Staphylococcus aureus* and methicillin-resistant *Staphylococcus aureus* in positive blood cultures," J. Clin. Microbiol. 45:2191-2196 (May 2007).
Sratidis et al., Use of real-time polymerase chain reaction for identication of methicillin-resistant *Staphylococcus aureus* directly from positive blood culture bottles, Diagn. Microbiol. Infect. Dis. 58:199-902 (2007).
Tang et al., "StaphPlex system for rapid and simultaneous identification of antibiotic resistance determinants and Panton-Valentine leukocidin detection of *Staphylococci* from positive blood cultures," J. Clin. Microbiol. 45:1867-1873 (Jun. 2007).
Vanguilder et al., "Twent-five years of quantitative PCR for gene expression analysis," BioTechniques 44:619-626 (2008).
Whitcombe et al., "Detection of PCR products using self-probing amplicons and fluorescence," Nature Biotechnol. 17:804807 (1999).
Chinese Application No. 200880123825.5, filed Dec. 19, 2008; Office Action mailed Jan. 28, 2014.
Israeli Application No. 206499, filed Dec. 19, 2008; Office Action mailed Jan. 10, 2014.
European Application No. 13169580.1, filed May 28, 2013; extended European search report mailed Oct. 1, 2013.
European Application No. 13169580.1, filed May 28, 2013; Office Action mailed Apr. 29, 2014.
European Application No. 13169580.1, filed May 28, 2013; Third Party Observations mailed May 12, 2014.
Opposition to European Patent No. 2231869 by Euroimmun Medizinische Labordiagnostika AG mailed Mar. 20, 2014.
Opposition to European Patent No. 2231869 by James Poole Limited mailed Mar. 20, 2014.
Opposition to European Patent No. 2231869 by Strawman Limited mailed Mar. 20, 2014.
U.S. Appl. No. 60/962,816, filed Jul. 31, 2007.
U.S. Appl. No. 60/907,848, filed Apr. 19, 2007.
U.S. Appl. No. 12/339,471, filed Dec. 19, 2008; Office Action mailed Jun. 8, 2011.
U.S. Appl. No. 12/339,471, filed Dec. 19, 2008; Office Action mailed Nov. 8, 2011.
U.S. Appl. No. 12/339,471, filed Dec. 19, 2008; Office Action mailed Apr. 25, 2012.
Australian Application No. 2008343878, filed Dec. 19, 2008; Office Action mailed Jul. 12, 2013.
Chinese Application No. 200880123825.5, filed Dec. 19, 2008; Office Action mailed Jul. 10, 2013.
Japanese Application No. 2010-539500, filed Dec. 19, 2008; Office Action mailed Jul. 10, 2013.
BioHelix, IsoAmp® Rapid mecA Detection Kit Manual for Research Use Only Catalog #D0200E, retrieved from the Internet May 5, 2013 at URL http://www.biohelix.com/pdf/D0200E_mecA_eDatacard.pdf.
BioHelix, IsoAmp® Rapid Staph Detection Kit Manual for Research Use Only Catalog #D0100E, retrieved from the Internet May 5, 2013 at URL http://www.biohelix.com/pdf/D0100E_SA_eDatacard.pdf.
Bishop et al., "Concurrent Analysis of Nose and Groin Swab Specimens by the IDI-MRSA PCR Assay Is Comparable to Analysis by Individual-Specimen PCR and Routine Culture Assays for Detection of Colonization by Methicillin-Resistant *Staphylococcus aureus*," J. Clin. Microbiol. 44(8):2904-2908 (2006).
Brown et al., "Real-Time PCR Detection of *S. aureus* and MRSA from Wound, Fluid and Respiratory Samples," Abstract No. C-077. American Society for Microbiology Conference, Orlando, Florida, May 21-25, 2006.
Chinese Patent Application No. 200880123825.5, Filed: Dec. 19, 2008; office action mailed Jun. 5, 2012.
Chinese Second Office Action Corresponding to Chinese Patent Application No. 200880123825.5; Date of Notification: Dec. 26, 2012; 7 Pages.
Cuny et al., "PCR for the identification of methicillin-resistant *Staphylococcus aureus* (MRSA) strains using a single primer pair specific for SCC*mec* elements and the neighbouring chromosome-borne *ortX*," Clin. Microbiol. Infect. 11:834-837 (2005).
Desjardins et al., "Evaluation of the IDI-MRSA Assay for Detection of Methicillin-Resistant *Staphylococcus aureus* from Nasal and Rectal Specimens Pooled in a Selective Broth," J. Clin. Microbiol. 44(4):1219-1223 (2006).
Donnio et al., "Partial Excision of the Chromosomal Cassette Containing the Methicillin Resistance Determinant Results in Methicillin-Susceptible *Staphylococcus aureus*," J. Clin. Microbiol. 43(8):4191-4193 (2005).
Drews, et al., "Verification of the IDI-MRSA Assay for Detecting Methicillin-Resistant *Staphylococcus aureus* in Diverse Specimen Types in a Core Clinical Laboratory Setting," J. Clin. Microbiol. 44(10):3794-3796 (2006).
European Application No. 08868000.4, filed Dec. 19, 2008; extended European search report mailed Feb. 28, 2011.
European Application No. 08868000.4, filed Dec. 19, 2008; office action mailed Jan. 13, 2012.
Goldmeyer, J. et al., "Identification of *Staphylococcus aureus* and Determination of Methicillin Resistance Directly from Positive Blood Cultures by Isothermal Amplification and a Disposable Detection Device", *Journal of Clinical Microbiology*, Apr. 2008, vol. 46, No. 4, 1534-1536.
Hagen et al., "Development of a real-time PCR assay for rapid identification of methicillin-resistant *Staphylococcus aureus* from clinical Samples," Int. J. Med. Microbiol. 295:77-86 (2005).
Holfelder et al., "Direct detection of methicillin-resistant *Staphylococcus aureus* in clinical specimens by a nucleic acid-based hybridisation assay," Clin. Microbiol. Infect. 12:1163-1167 (2006).
Huletsky et al., "Identification of methicillin-resistant *Staphylococcus aureus* carriage in less than 1 hour during a hospital surveillance program," Clin. Infect. Dis. 40:976-981 (2005).
Huletsky et al., New Real-Time PCR Assay for Rapid Detection of Methicillin-Resistant *Staphylococcus aureus* Directly from Specimens Containing a Mixture of Staphylococci, J. Clin. Microbiol. 42(5):1875-1884 (2004).
International Search Report and Written Opinion, PCT/US08/13922, mailed Aug. 5, 2009.
Israeli Patent Application No. 206499; Filed: Dec. 19, 2008; office action mailed Mar. 5, 2012.
Ito T. et al., "Guidelines for Reporting Novel mecA Gene Homologues", Antimicrob. Agents Chemother. Published online ahead of print on Aug. 6, 2012, 9 pages.

(56) References Cited

OTHER PUBLICATIONS

Laurent F. et al., "MRSA Harboring mecA Variant Gene mecC, France", Emerging Infectious Diseases, vol. 18, No. 9, Sep. 2012; 1465-1467.

Lowe et al., Nucleic acid research, 1990, vol. 18(7), p. 1757-1761.

Rupp et al., "Be Aware of the Possibility of False-Positive Results in Single-Locus PCR Assays for Methicillin-Resistant *Staphylococcus aureus*," *J. Clin. Microbiol.* 4(6):2317 (2006).

Warren et al., "Detection of Methicillin-Resistant *Staphylococcus aureus* Directly from Nasal Swab Specimens by a Real-Time PCR Assay," *J. Clin. Microbiol.* 42(12):5578-5581 (2004).

Zhang et al., "Novel multiplex PCR assay for characterization and concomitant subtyping of staphylococcal cassette chromosome mec types I to V in methicillin-resistant *Staphylococcus aureus*," J. Clin. Microbiol. 43:5026-5033 (2005).

European Application No. 13169580.1, filed May 28, 2013; Office Action mailed Feb. 2, 2015.

European Application No. 13169580.1, filed May 28, 2013; Third Party Observations mailed Jan. 9, 2015.

European Patent No. 2231869; Third Party Observations mailed Feb. 24, 2015.

Japanese Application No. 2014-050190, filed Mar. 13, 2014; Translation of Jun. 2, 2015 Office Action mailed Jul. 10, 2015.

Japanese Application No. 2014-050190, filed Mar. 13, 2014; Office Action mailed Oct. 2, 2015.

Translation of Japanese Application No. 2014-050190, filed Mar. 13, 2014; Office Action mailed Oct. 2, 2015.

Australian Application No. 2014203649, filed Jul. 3, 2014; Office Action mailed Dec. 17, 2015.

Chinese Application No. 200880123825.5, filed Jul. 2, 2010; Office Action mailed Nov. 25, 2015.

European Application No. 13169580.1, filed May 28, 2013; Office Action mailed Oct. 23, 2015.

\* cited by examiner

NASBA approach 1

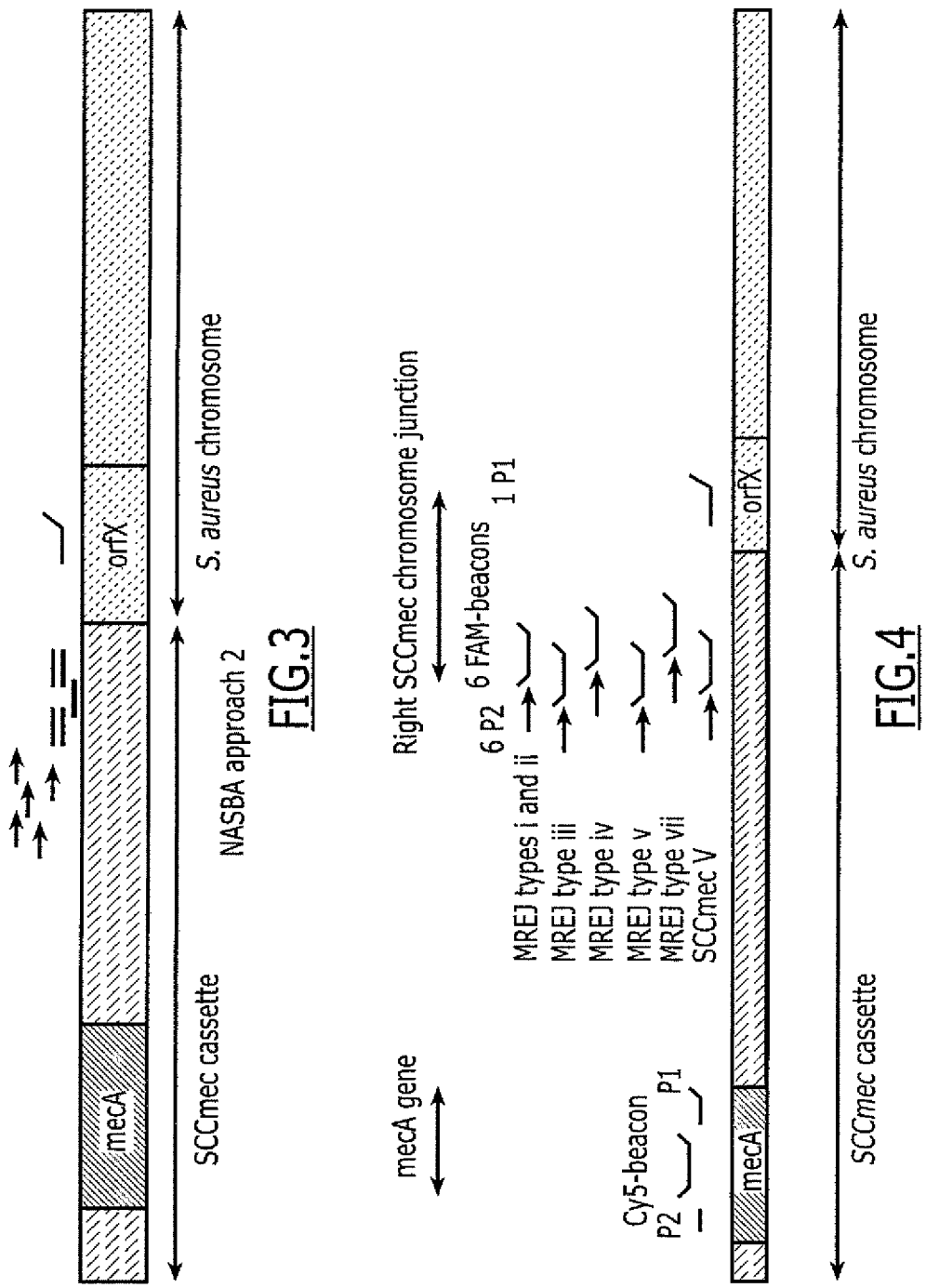

DETECTION OF METHICILLIN-RESISTANT *STAPHYLOCOCCUS AUREUS*

STATEMENT OF PRIORITY

This application is a continuation of U.S. application Ser. No. 12/339,471, filed Dec. 19, 2008, which claims the benefit, under 35 U.S.C. §119(e), of U.S. Provisional Application No. 61/008,680, filed Dec. 21, 2007, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821(h), entitled 9250-174CT_seqListing.txt, 5120 bytes in size, generated on Mar. 25, 2013 and filed via EFS-Web, is provided in lieu of a paper copy. This Sequence Listing is hereby incorporated by reference into the specification for its disclosures.

FIELD OF THE INVENTION

The present invention relates to molecular detection of methicillin-resistant *Staphylococcus aureus* (MRSA). More particularly, the present invention relates to an improved detection of MRSA that reduces false positive results.

BACKGROUND OF THE INVENTION

Methicillin-resistant *Staphylococcus aureus* (MRSA) is a major nosocomial but also community acquired pathogen that can cause serious infections such as surgical wound infections, pneumonia, endocarditis and septicemia. Resistance to methicillin is due to the presence of the mecA gene that encodes a modified Penicillin-Binding protein, PBP2a or PBP2', with reduced affinity for B-lactam drugs. The mecA gene is carried by a cassette named the SCCmec (Staphylococcal Cassette Chromosome mec; Ito et al., 2001, Antimicrob. Agents Chemother. 45(5):1323-1336; Hiramatsu, et al., 2001, Trends Microbiol. October; 9(10):486-93), a mobile element that can be incorporated into the chromosome of *S. aureus* and other coagulase negative Staphylococci, mainly *S. epidermidis* and *S. haemolyticus*. SCCmec is characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). The site of insertion of this mecA gene cassette SCCmec into the *Staphylococcus aureus* genome is known and the sequence conserved (Ito et al., 2001, Antimicrob. Agents Chemother. 45:1323-1336). After insertion into the *S. aureus* chromosome, the SCCmec has a left extremity junction region and a right extremity junction region (see FIG. 1), where the SCCmec sequence is contiguous with the *S. aureus* chromosomal sequence. The nucleotide sequence of the regions surrounding the left and right boundaries of SCCmec DNA (i.e. attL and attR, respectively), as well as those of the regions around the SCCmec DNA integration site (i.e., attBscc, the bacterial chromosome attachment site for SCCmec DNA), have previously been analyzed. Sequence analysis of the integration sites revealed that attBscc is located at the 3' end of a novel open reading frame (ORF), orfX. orfX encodes a putative 159-amino acid polypeptide that exhibits sequence homology with some previously identified polypeptides of unknown function (Ito et al., 1999, Antimicrob. Agents Chemother. 43:1449-1458). Organization of the mecA region of SCCmec has additionally been studied (Oliveira, D. C., et al., 2000, Antimicrob. Agents Chemother. 44(7):1906-1910).

MRSA can be carried by healthy people without causing any disease but these healthy carriers, when entering the hospital, can contaminate hospitalized patients. Additionally, a patient can contaminate himself, e.g., if one undergoes surgery, the risk of infection is increased. MRSA healthy carriers constitute a reservoir of MRSA and screening of these carriers must be performed to eradicate the strains by local decontamination. MRSA screening is now recognized as a major tool to reduce the prevalence of MRSA strains in the world. Typically, in an MRSA assay in a patient, a nasal swab is taken from the patient and cultured repeatedly, to determine if an MRSA strain is present. The need to culture could be obviated by an assay for identifying MRSA directly from a nasal swab. Culture identification methods typically require minimally 24 hours, and more typically 72 hours, to obtain results. New chromogenic media (having substrate(s) within the media and, typically, antibiotic (e.g., cefoxitin) to select methicillin-resistant strains) can potentially restrict this time to result to a 24-48 hour time period. However, in the case of MRSA infection, results are needed in a matter of hours, since the patient should be isolated until results are obtained. Therefore, a reliable molecular MRSA test which can provide results in a matter of 2-4 hours is highly desirable.

Amplification is a well known art, and various methods have been developed, including transcription-based amplification such as transcription-mediated amplification (TMA; U.S. Pat. Nos. 5,766,849 5,399,491; 5,480,784; 5,766,849; and 5,654,142) and nucleic acid sequence-based amplification (NASBA; 5,130,238; 5,409,818; 5,654,142; and 6,312, 928), and cycling nucleic acid amplification technologies (thermocycling) such as polymerase chain reaction (PCR; U.S. Pat. Nos. 4,683,195; 4,965,188; 4,683,202) and ligase chain reaction (LCR; U.S. Pat. No. 5,792,607). Known amplification methods also include strand displacement amplification (SDA), self-sustained sequence replication (3SR), Q-β replicase, and cascade rolling circle amplification (CRCA).

Detection methods utilizing nucleic acids are also well known in the art. Nucleic acids are often labeled for various detection purposes. For example, methods described in U.S. Pat. No. 4,486,539 (Kourlisky); U.S. Pat. No. 4,411,955 (Ward); U.S. Pat. No. 4,882,269 (Schneider) and U.S. Pat. No. 4,213,893 (Carrico), illustrate preparation of labeled detection probes for detecting specific nucleic acid sequences. Probe designs for different detection methods, such as target-capture, HPA, TAQman, molecular beacons and sandwich hybridization have also been described (e.g., U.S. Pat. No. 4,486,539, and U.S. Pat. Nos. 4,751,177; 5,210, 015; 5,487,972; 5,804,375; 5,994,076). Nucleic acid hybridization techniques and conditions are known to the skilled artisan and have been described for example, in Sambrook et al. Molecular Cloning A Laboratory Manual, 2nd Ed. Cold Spring Lab. Press, December 1989; U.S. Pat. No. 4,563,419 (Ranki) and U.S. Pat. No. 4,851,330 (Kohne) and in Dunn, et al., *Cell* 12, pp. 23-26 (1978) among many other publications. Probe designs for different detection methods are also known, such as target-capture, HPA, TaqMan, molecular beacons and sandwich hybridization (e.g., U.S. Pat. No. 4,486,539, and U.S. Pat. Nos. 4,751,177; 5,210,015; 5,487,972; 5,804,375; 5,994,076).

Earlier molecular methods developed to detect and identify MRSA based on the detection of the mecA gene and *S. aureus*-specific chromosomal sequences have been described. (Saito et al., 1995, J. Clin. Microbiol. 33:2498-

2500; Ubukata et al., 1992, J. Clin. Microbial. 30:1728-1733; Murakami et al., 1991, J. Clin. Microbiol, 29:2240-2244; Hiramatsu et al., 1992, Microbial. Immunol. 36:445-453). However, positive results for the presence in a sample of both mecA gene and *S. aureus* chromosomal sequences cannot guarantee MRSA is present, since, for example, in tests based on the detection of mecA and *S. aureus* specific marker, false positives can be observed in the presence of MSSA and methicillin resistant coagulase negative *Staphylococcus* that possess the mecA gene. Furthermore, in tests based on the detection of the cassette junction only, false positives have been observed with methicillin-susceptible *S. aureus* isolates containing a small fragment of the right extremity of the SCCmec (see Rupp, J. et al., J. Clin. Microbiol. 44(6): 2317 (2006)). Additionally, Ramakrishnan and Riccelli describe a method for detecting MRSA utilizing oligonucleotide probes having sequences that are complementary to regions near the left junction of the SCCmec cassette insertion site, including part of the SCCmec cassette sequence and part of the *S. aureus* sequence in the region of insertion (the left extremity junction region) (U.S. patent publication No. US20060057613).

However, previous attempts to determine MRSA by molecular methods have had difficulties with false positive results. Such results have been postulated to be the result of any of the presence of a mixed population in swabs, the presence in an MSSA of a residual SCCmec right extremity fragment following the deletion of the mecA gene and/or non-specific amplification. To date, two concepts for determining resistance to methicillin carried specifically by *S. aureus* have been published:

the SCCmec right extremity junction amplification concept (Hiramatsu et al. WO97/31125; EP 0 887 424; U.S. Pat. No. 6,156,507; and further, Huletsky and Rossbach WO02/099034 (2002); Huletsky et al. *J. Clin. Microbiol.* 42(5): 1875-1884 (2004))

the immuno-enrichment concept described by François and co-workers (François, P et al. *J. Clin. Microbiol.* 41(1): 254-260 (2003); WO02/082086), in which the immuno-enrichment is followed by amplification of three markers (mecA gene, *S. aureus*-specific marker, and *S. epidermidis*-specific marker).

The SCCmec right extremity junction concept is based on the amplification of a region covering the right extremity junction region of the SCCmec integration site. The principle is the following: the SCCmec cassette always integrates the *S. aureus* chromosome upstream of a *S. aureus* specific open reading frame called orfX; the PCR assay combines multiple forward primers located on the right part of the cassette, one reverse primer and a beacon probe, both located in the *S. aureus* chromosomal orfX, i.e., downstream of the right extremity junction of SCCmec with orfX ("right extremity junction region" of orfX). Hiramatsu et al, describe a test with two forward primers in the right extremity junction region of the cassette to amplify the main SCCmec types described at that time (one primer for SCCmec types I and II and a second primer for type III). Huletsky et al. set forth that several MRSA strains were not detected if only the two forward primers described by Hiramatsu were used, and they determined new types of cassettes named as MREJ types having sequence variations in the right part of the SCCmec cassette. A commercially available (Infectio Diagnostics Inc.) test combines (refer to FIG. 1) five forward primers located in the right part of the cassette (one primer was designed for the detection of MREJ types i and ii and the four others for the MREJ types iii, iv, v and vii), one reverse primer located in the orfX, and three generic beacons covering the same portion of the orfX region and required to identify the orfX variants identified. This test is performed in real-time PCR. However, the specificity of this test as reported (Huletsky et al. 2004) shows that 4.6% of MSSA (26 out of 569 tested) were misidentified. False-positive result has also been reported with another commercial test using a single-locus (right extremity SCCmec cassette-orfX junction) PCR assay (Rupp, J, et al.,*J. Clin. Microbiol.* (44)6: 2317 (2006)).

Thus false positives remain an issue, and there is a strong need for an improved test for MRSA to reduce false positive results obtained with current tests. The challenge for such a test is that, due to the presence of a mixed population in nasal swabs, the following mixtures can be present: one or more of (1) MRSA, (2) methicillin sensitive coagulase-negative Staphylococci (e.g., methicillin sensitive *Staphylococcus epidermidis* (MSSE)), (3) methicillin sensitive *Staphylococcus aureus* (MSSA), and (4) methicillin resistant coagulase-negative Staphylococci (MR-CNS) (mainly methicillin resistant *Staphylococcus epidermidis* (MRSE)). Furthermore, there has been report of clinical MSSA isolates retaining SCCmec elements without the mecA gene. (Donnio, P.-Y., et al., J Clin Microbiol. 2005 August; 43(8): 4191-4193). Because only the presence of a MRSA will lead to decontamination of the carrier, the test must ensure that resistance to methicillin is carried by *S. aureus* and not by *S. epidermidis* (or coagulase (-) *Staphylococcus* strain). Thus, also, amplification and detection of the mecA gene (associated or not with a *S. aureus* specific marker) directly on the mixed population present on the swabs is not appropriate; indeed in both situations (MRSA+MSSE or MSSA+MRSE), both markers (mecA and *S. aureus* specific marker) will be detected whereas only the first situation with an MRSA is desired to be specifically detected by the clinician. The present invention addresses primary sources of MRSA false positives and thus provides a much-needed, improved test to detect MRSA that has not been addressed by currently available tests.

SUMMARY OF THE INVENTION

The present invention provides a method of detecting in a sample a methicillin-resistant *Staphylococcus aureus* (MRSA) having an insertion of an SCCmec cassette within *Staphylococcus aureus* chromosomal DNA, comprising performing on the sample an amplification and detection reaction utilizing a. a first primer capable of specifically hybridizing in an extremity junction region of the SCCmec cassette, b. a second primer capable of specifically hybridizing in an extremity junction region of chromosomal *Staphylococcus aureus* DNA, and c. a probe capable of specifically hybridizing to a region of the SCCmec cassette between the region with which the first primer is capable of hybridizing and the junction, wherein each of the first primer and the second primer is oriented such that, under amplification conditions, the junction is amplified, and wherein if the sample contains MRSA, hybridization of the probe is detected. In such methods as set forth herein, "a" primer, probe, etc. can mean one or more primer or probe, unless otherwise stated or the context dictates otherwise.

The present invention additionally provides a method of detecting in a sample a methicillin-resistant *Staphylococcus aureus* (MRSA) having an insertion of an SCCmec cassette within *Staphylococcus aureus* chromosomal DNA, comprising (a) performing on the sample an amplification and detection reaction that detects the presence of a junction of an inserted SCCmec cassette and *Staphylococcus aureus* chromosomal DNA utilizing
1) a first primer capable of specifically hybridizing in an extremity junction region of the SCCmec cassette,
2) a second primer capable of specifically hybridizing in an extremity junction region of chromosomal *Staphylococcus aureus* DNA, and
3) a first probe capable of specifically hybridizing to a region of the SCCmec cassette between the region with which the first primer is capable of hybridizing and the junction, wherein each of the first primer and the second primer is oriented such that, under amplification conditions, the junction is amplified, and
(b) performing on the sample an amplification and detection reaction that detects the presence of the mecA gene, wherein if the sample contains MRSA, the presence of both the target junction and mecA in the sample is detected.

The present invention further provides a method of detecting in a sample a methicillin-resistant *Staphylococcus aureus* (MRSA) having an insertion of an SCCmec cassette within *Staphylococcus aureus* chromosomal DNA, comprising performing on the sample a multiplex amplification reaction wherein the amplification reaction comprises
a. amplifying and detecting the presence of a junction of an inserted SCCmec cassette and *Staphylococcus aureus* chromosomal DNA utilizing
1) a first primer capable of specifically hybridizing in an extremity junction region of the SCCmec cassette,
2) a second primer capable of specifically hybridizing in an extremity junction region of chromosomal *Staphylococcus aureus* DNA, and
3) a first probe capable of specifically hybridizing to a region of the SCCmec cassette between the region with which the first primer is capable of hybridizing and the junction, wherein each of the first primer and the second primer is oriented such that, under amplification conditions, the junction is amplified, and
b. amplifying and detecting the presence of mecA gene, wherein if the sample contains MRSA, the presence of both the target junction and mecA in the sample is detected.

Additionally, the present invention provides a method of detecting in a sample a methicillin-resistant *Staphylococcus aureus* (MRSA) having an insertion of an SCCmec cassette within *Staphylococcus aureus* chromosomal DNA, the method comprising
a. performing on a sample an amplification reaction which can simultaneously amplify both (1) a junction of an inserted SCCmec cassette and *Staphylococcus aureus* chromosomal DNA and (2) a region of mecA, and
b. detecting, within the products of the amplification, the presence or absence of each of the junction and mecA, wherein if the sample contains MRSA, the presence of both the junction and mecA in the sample is detected.

The present invention further provides a method of identifying the presence in a sample of a methicillin-resistant *Staphylococcus aureus* (MRSA) having an insertion of an SCCmec cassette within *Staphylococcus aureus* chromosomal DNA which comprises the steps of:
bringing, in a single container, the biological sample in contact with
(a) a first oligonucleotide set comprising
(1) a first oligonucleotide having a nucleic acid sequence that specifically hybridizes to an extremity junction region of a SCCmec cassette, and
(2) a second oligonucleotide having a nucleic acid sequence that specifically hybridizes to a *Staphylococcus aureus* chromosomal DNA region flanking said SCCmec cassette to form a first reaction product of the biological sample and the first and second oligonucleotides, and
(b) a second oligonucleotide set comprising
(3) a third oligonucleotide having a nucleotide sequence that specifically hybridizes to a first region of mecA nucleic acid and
(4) a fourth oligonucleotide having a nucleotide sequence that specifically hybridizes to a second region of mecA nucleic acid to form a second reaction product of the biological sample and the third and fourth oligonucleotides; and identifying the presence of MRSA by detecting both a first and a second reaction product. The identifying step can, in one embodiment, comprise contacting the first and second reaction products with (1) a first probe capable of specifically hybridizing with the first reaction product and (2) a second probe capable of specifically hybridizing with the second reaction product.

The present invention additionally provides kits for use in such methods. Specifically, the present invention provides a kit for detection of methicillin-resistant *Staphylococcus aureus* (MRSA) having an insertion of an SCCmec cassette within *Staphylococcus aureus* chromosomal DNA, comprising
(a) a first primer capable of specifically hybridizing in an extremity junction region of the SCCmec cassette,
(b) a second primer capable of specifically hybridizing in chromosomal *Staphylococcus aureus* DNA in a region of the extremity junction, and
(c) a probe capable of specifically hybridizing fully within a region of the SCCmec cassette between the region with which the first primer is capable of hybridizing and the junction, wherein each of the first primer and the second primer is oriented such that, under amplification conditions, the junction is amplified. Further, the present invention provides a kit for identifying the presence in a sample of a methicillin-resistant *Staphylococcus aureus* (MRSA) having an insertion of an SCCmec cassette within *Staphylococcus aureus* chromosomal DNA which comprises:
a) first amplification and detection oligonucleotide set comprising
1) a first primer capable of specifically hybridizing in an extremity junction region of the SCCmec cassette,
2) a second primer capable of specifically hybridizing in chromosomal *Staphylococcus aureus* DNA in a region of the extremity junction, and
3) a first probe selected from the group consisting of (1) a first probe capable of specifically hybridizing primarily within a region of the SCCmec cassette between the region with which the first primer is capable of hybridizing and the junction, and (2) a first probe capable of specifically hybridizing fully within a region of the SCCmec cassette between the region with which the first primer is capable of hybridizing and the junction,
wherein each of the first primer and the second primer is oriented such that, under amplification conditions, the junction is amplified, and
b) a second amplification and detection oligonucleotide set comprising
4) a third primer capable of specifically hybridizing to a first region of mecA, 5) a fourth primer capable of specifically hybridizing to a second region of mecA, and
6) a second probe capable of specifically hybridizing to a region of mecA between the first and second regions of mecA, wherein each of the third primer and the fourth primer is oriented such that, under amplification conditions, the region of mecA between the first and second regions of mecA is amplified.

BRIEF DESCRIPTION OF THE DRAWINGS

FIG. 3 demonstrates generally the location of primers and probes for an inventive method for detection of the right extremity junction of the SCCmec insertion in MRSA: five Primers 2 ("P2," arrows) located in SCCmec right extremity junction region, Primer 1 ("P1," angled line) located in orfX, and five specific probes (lines) located in the right part of the SCCmec cassette are used ("Approach 2").

FIG. 4 demonstrates multiplex amplification of mecA and the right extremity junction with the following primers and probes: in mecA, Primer 1 ("P1"), Primer 2 ("P2") and probe ("beacon"); in "Right SCCmec-chromosome junction region," right extremity junction region, Primer 1 ("1P1," angled line), five Primers 2 ("5P2," arrows) and five SCCmec-specific probes ("5 specific beacons," lines angled at both ends).

DETAILED DESCRIPTION OF THE INVENTION

Figure 2:
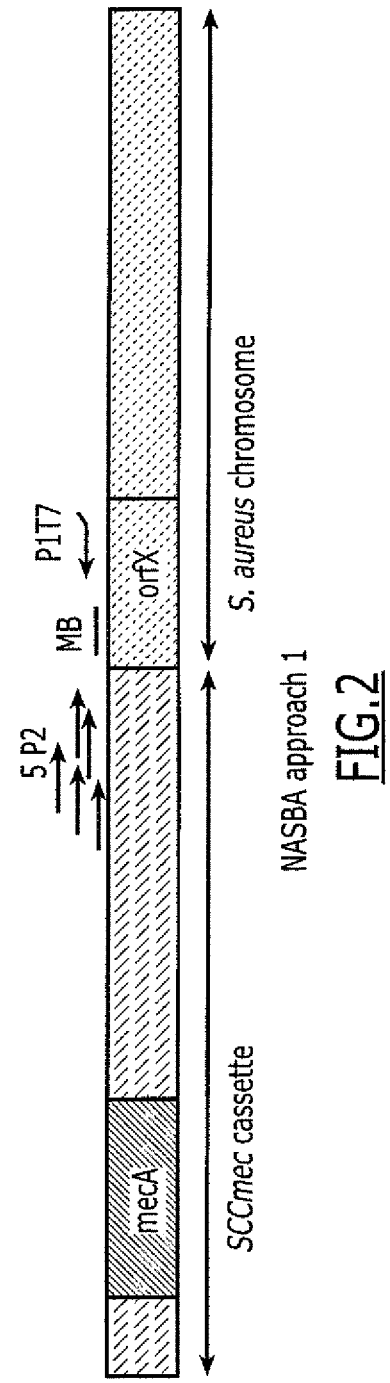
FIG. 2 demonstrates generally the location of primers and probes in the right extremity junction region of SCCmec/orfX wherein five Primers 2 ("5P2," arrows) are located in the right part of the cassette, one generic Primer 1 ("P1T7") is located in S. aureus orfX and one generic beacon ("MB") is located in S. aureus orfX ("Approach 1").

As discussed herein, the present invention provides that the identification of false positives by the previous molecular methods can be explained in some instances by the presence in MSSA strains of a residual SCCmec right extremity fragment following the deletion of a chromosomal region containing mecA or the presence of an SCC which does not contain mecA. Additionally, as further disclosed herein, the present invention provides that some portion of the false positives can be due to non specific amplification; indeed, (as shown in FIG. 2) because the reverse primer and the beacons are located in the orfX which is common to both MRSA and MSSA, non specific annealing of the forward primer(s) on MSSA chromosome will lead to amplification and detection of MSSA. The present invention addresses both sources of false positives and provides an improved test.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described.

As used herein and in the appended claims, the singular forms "a", "an", and "the" include plural reference unless the context clearly dictates otherwise.

As stated above, the present invention provides solutions to reduce the lack of specificity due to MSSA detection reported with previous detection methods, which solutions can be utilized individually or, ideally, within the same test. Thus, the present invention describes the use of specific beacons (specific for SCCmec cassette) rather than generic beacons; this configuration will suppress detection of MSSA amplified due to non-specific amplification. Further, the present invention describes the advantage of combining in multiplex reaction the mecA gene detection with the cassette insertion region (e.g., Right SCCmec-chromosome junction region) detection, compared to the detection of the cassette insertion region alone; this aspect of the invention can reduce detection of MSSA either due to presence of a residual SCCmec right extremity fragment following the deletion of a chromosomal region containing mecA or to the presence of an SCC which does not contain mecA.

In a preferred embodiment, the present invention provides a method of detecting in a sample a methicillin-resistant *Staphylococcus aureus* (MRSA) having an insertion of an SCCmec cassette within *Staphylococcus aureus* chromosomal DNA, comprising
performing on the sample an amplification and detection reaction utilizing
  a. a first primer capable of specifically hybridizing in an extremity junction region of the SCCmec cassette,
  b. a second primer capable of specifically hybridizing in an extremity junction region of chromosomal *Staphylococcus aureus* DNA, and
  c. a probe capable of specifically hybridizing to a region of the SCCmec cassette between the region with which the first primer is capable of hybridizing and the junction,
wherein each of the first primer and the second primer is oriented such that, under amplification conditions, the junction is amplified, and wherein if the sample contains MRSA, hybridization of the probe is detected.

The genomic structure of MRSA has been characterized previously. As used in the claims, the "SCCmec cassette" (sometimes referred to as "mecDNA," e.g., in Hiramatsu U.S. Pat. No. 6,156,507) has the definition as known in the art, i.e., an integrated adventitious DNA existing on a chromosome of MRSA or MR-CNS and including the mec gene complex, a set of site-specific recombinase genes (ccrA and ccrB), and terminal inverted and direct repeats (at both 3' and 5' ends). "mecA gene" includes all sequences necessary to encode PBP2a or PBP' (Penicillin Binding Protein) conferring methicillin resistance.

Figure 1:
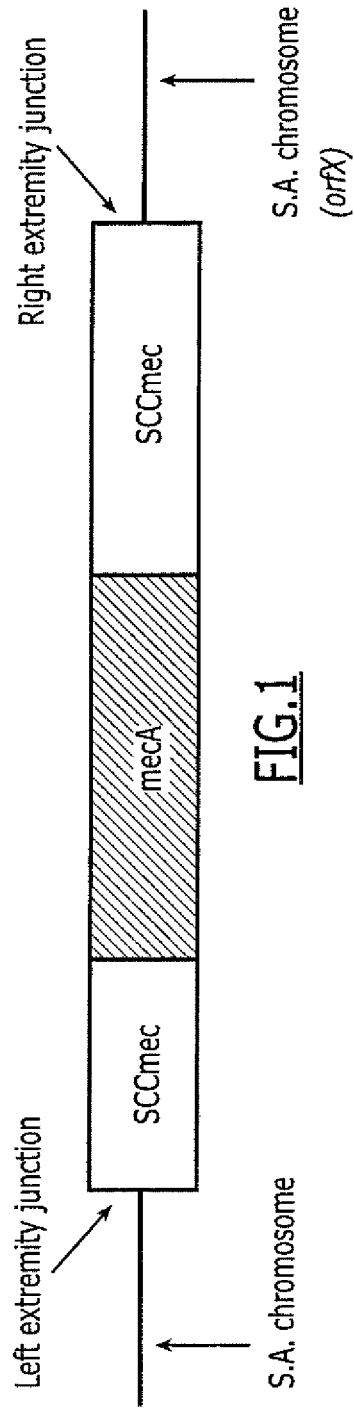
FIG. 1 shows generally the region of MRSA chromosome with the inserted SSCmec cassette, indicating the left and right extremity junctions.

As known in the art, insertion of the SCCmec cassette into the S. aureus chromosome creates two junctions, and two corresponding junction regions, of SCCmec DNA with S. aureus chromosomal DNA, wherein the SCCmec sequence is contiguous with the S. aureus chromosomal sequence. The junctions, therefore, are located at the left and right extremities of the SCCmec cassette (see FIG. 1). These two regions are named "Right SCCmec-Chromosome Junction" and "Chromosome-Left SCCmec junction" by Ito et al. (Antimicrob. Agents Chemother. May 2001 45(5): 1323-1336, "Structural Comparison of three Types of Staphylococcal Cassette Chromosome mec Integrated in the chromosome in Methicillin-Resistant *Staphylococcus aureus*"). At the right extremity junction, the *S. aureus* genomic sequence abutting the SCCmec cassette is the gene orfX, which is in some literature referred to as "IntM." As used in the claims, "extremity junction region" is a region of either SCCmec cassette or *S. aureus* chromosomal nucleic acid within distance of either the right or the left extremity junction, or insertion site, such that a primer can, in a primer extension reaction or a transcription-type (e.g., NASBA or TMA) reaction, be extended across that junction, e.g., within 600 nt, 550 nt, 500 nt, 450 nt, 400 nt, 350 nt, 300 nt, 250 nt, 200 nt, 150 nt, 100 nt, or 50 nt (in either direction) of the junction. Useful distances may vary depending upon the amplification technology used (e.g., it may be longer distances as new technologies are developed). "Extremity junction region," therefore, depending upon context used, can refer to a region within the SCCmec DNA or a region within the *S. aureus* chromosomal DNA; both uses refer to such DNA within distance of the junction such that an appropriately selected primer could, under appropriate, standard extension or amplification conditions, be extended, or transcribed, from it, in the direction of the junction, across the junction. That is, "an extremity junction region of the SCCmec cassette" would be a region within the SCCmec DNA near its abutment, or integration site, with the *S. aureus* chromosomal DNA; and "an extremity junction region of orfX" would be a region within the orfX DNA near an abutment with SCCmec DNA (an SCCmec integration site). Similarly, "an extremity junction region of chromosomal *S. aureus* DNA" would be a region within the chromosomal *S. aureus* DNA near an abutment with SCCmec DNA. Alternatively, this region may also be referred to as "chromosomal *S. aureus* DNA in the region of the SCCmec extremity junction." Thus, "right extremity junction region" refers to the region surrounding the junction on the right side of the SCCmec cassette, and "left extremity junction region" refers to the region surrounding the junction on the left side of the SCCmec cassette (see FIG. 1).

To further provide a useful method for detecting MRSA, the present invention provides an amplification and detection which detects both the presence of a SCCmec insertion junction and mecA sequences. More specifically, the present invention additionally provides a method of detecting in a sample a methicillin-resistant *Staphylococcus aureus* (MRSA) having an insertion of an SCCmec cassette within *Staphylococcus aureus* chromosomal DNA, comprising
(a) performing on the sample an amplification and detection reaction that detects the presence of a junction of an inserted SCCmec cassette and *Staphylococcus aureus* chromosomal DNA utilizing
   1) a first primer capable of specifically hybridizing in an extremity junction region of the SCCmec cassette,
   2) a second primer capable of specifically hybridizing in an extremity junction region of chromosomal *Staphylococcus aureus* DNA, and
   3) a first probe capable of specifically hybridizing to a region of the SCCmec cassette between the region with which the first primer is capable of hybridizing and the junction,
wherein each of the first primer and the second primer is oriented such that, under amplification conditions, the junction is amplified, and
(b) performing on the sample an amplification and detection reaction that detects the presence of mecA gene,
   wherein if the sample contains MRSA, the presence of both the target junction and mecA in the sample is detected.
Such a method is particularly helpful in discriminating MRSAs from those, somewhat rare, MSSAs from which mecA, but not the complete SCCmec cassette, have been deleted.

Advantageously, one can perform a multiplex amplification reaction to detect both the presence of a SCCmec insertion junction and mecA sequences. Thus, the present invention provides a method of detecting in a sample a methicillin-resistant *Staphylococcus aureus* (MRSA) having an insertion of an SCCmec cassette within *Staphylococcus aureus* chromosomal DNA, comprising
   performing on the sample a multiplex amplification reaction wherein the amplification reaction comprises
   a. amplifying and detecting the presence of a junction of an inserted SCCmec cassette and *Staphylococcus aureus* chromosomal DNA utilizing
     1) a first primer capable of specifically hybridizing in an extremity junction region of the SCCmec cassette,
     2) a second primer capable of specifically hybridizing in an extremity junction region of chromosomal *Staphylococcus aureus* DNA, and
     3) a first probe capable of specifically hybridizing to a region of the SCCmec cassette between the region with which the first primer is capable of hybridizing and the junction,
   wherein each of the first primer and the second primer is oriented such that, under amplification conditions, the junction is amplified, and
   b. amplifying and detecting the presence of mecA gene,
wherein if the sample contains MRSA, the presence of both the target junction and mecA in the sample is detected.

By "amplify the junction" is meant performing an amplification reaction that produces an amplification product that includes sequences corresponding to nucleic acids both within SCCmec abutting the junction and within *S. aureus* chromosomal DNA abutting the same junction. By "amplifying and detecting the presence of mecA gene" is meant amplifying and detecting within the sample any portion of a mecA gene, for example, the region between primers comprising a nucleic acid sequence set forth in SEQ ID NO: 15 and 16 (which can be detected, for example, utilizing a probe comprising the nucleic acid sequence set forth in SEQ ID NO: 14). Primers and probes can be readily designed for hybridization to the known mecA sequence.

The term "multiplex amplification reaction" means that the specific reagents for amplification of more than one target are contacted together, such that more than one amplification can occur within the same reaction container. Additionally, detection reagents for more than one target can be included. Thus one can conduct a multiplex amplification and detection reaction by placing into contact all of the specific reagents for amplification and detection of more than one target. Thus, in a multiplex reaction, one can amplify multiple target regions in the same reaction. "Simultaneous amplification" wherein individual reactions are allowed to proceed at the same time, but the reactants for more than one amplification reaction are not necessarily all within the same reaction container, or tube, rather, the more than one reactions can be carried out in separate reaction containers, can also be utilized if a multiplex is not desired or feasible. It is understood that, even in a multiplex amplification reaction, each reaction will occur at whatever pace the individual reactions proceed under the provided conditions. Detection can also be "simultaneous," meaning that, if appropriate probes for each reaction in the reaction container are included, under the appropriate conditions, detection of more than one target can be achieved in either a single reaction container (multiplex) or in more than one reaction container (appropriate probes distributed to the relevant reaction container). Such detection can be performed, if desired, in the same reaction container as the multiplex or simultaneous amplification reaction, and, further, can be performed while amplification reactions continue (i.e., real-time).

Thus, the present invention provides a method of detecting in a sample a methicillin-resistant *Staphylococcus aureus* (MRSA) having an insertion of an SCCmec cassette within *Staphylococcus aureus* chromosomal DNA, the method comprising a. performing on a sample a multiplex amplification reaction which can amplify both (1) a junction of an inserted SCCmec cassette and *Staphylococcus aureus* chromosomal DNA and (2) a region of mecA, and b. detecting, within the products of the amplification, the presence or absence of each of the junction and mecA, wherein if the sample contains MRSA, the presence of both the junction and mecA in the sample is detected.

Amplification of the junction of an inserted SCCmec cassette and *Staphylococcus aureus* chromosomal DNA can be advantageously achieved by utilizing 1) a first primer capable of specifically hybridizing in an extremity junction region of the SCCmec cassette,
2) a second primer capable of specifically hybridizing in an extremity junction region of chromosomal *Staphylococcus aureus* DNA, and
3) a first probe capable of specifically hybridizing to a region of the SCCmec cassette between the region with which the first primer is capable of specifically hybridizing and the junction, wherein each of the first primer and the second primer is oriented such that, under amplification conditions, the junction is amplified. This probe can be selected to specifically hybridize fully within the SCCmec region. The presence or absence of either the junction or mecA can be determined by performing whatever analysis provides detection of the product, e.g., if a labeled probe is used, detection of the hybridized label by the appropriate detection device. Lack of a detectable signal indicates the absence of the target; perception of a detectable signal indicates presence of the target.

Primers and probes used in a reaction of this invention are capable of specifically hybridizing with a target nucleic acid. Specific hybridization is known in the art, and, typically, specific hybridization is achieved through nucleic acid identity or high similarity of the primer/probe with the target nucleic acid and/or through use of stringent hybridization conditions (e.g., stringent temperature and/or salt conditions). Specific hybridization provides selective hybridization to the target within the reaction.

A primer "oriented such that, under amplification conditions, the junction is amplified" includes a primer oriented such that, upon hybridization to its specific target nucleic acid, and upon initiation of an amplification reaction including the primer, an amplicon is formed that includes the junction. Such a reaction is designed to amplify across the junction (i.e., to be in sufficiently close proximity of the junction so that a typical amplification reaction would extend across the junction). Thus a primer pair useful for amplifying a junction will typically hybridize to two regions that surround the junction and each primer will be oriented to hybridize in a 5'-3' direction toward the junction. Typically, the primer would be designed to hybridize within 600 nt, 500 nt, 400 nt, 350 nt, 300 nt, 250 nt, 200 nt 150 nt, 100 nt, 50 nt, 30 nt, 25 nt, 20 nt, etc. of the junction. A probe for detecting an amplification product is therefore selected to be capable of specifically hybridizing to a region of the SCCmec cassette between the region with which the first primer is capable of hybridizing and the junction. In certain embodiments, such a probe can specifically hybridize fully within or primarily within SCCmec cassette. In one embodiment, in which the probe specifically hybridizes primarily within SCCmec cassette, the region to which the probe hybridizes can additionally include the junction and, therefore, at least one, or two or three or a few nucleotides of orfX that abut the junction. If one, two three or a few nucleotides of the probe hybridize to a region of orfX abutting the junction, the probe will, however, be capable of at least 75%, at least 80%, at least 85%, at least 90%, at least 91%, at least 92%, at least 93%, at least 94%, at least 95%, at least 96%, at least 97%, at least 98%, or at least 99% of its nucleotides, preferably contiguous, specifically hybridizing to a region of the SCCmec cassette between the region with which the first primer is capable of hybridizing and the junction. Thus, for an amplification of the right extremity junction region, the probe is selected to specifically hybridize to a region of the SCCmec cassette that is 3', or downstream, of the 3' end of the SCCmec cassette primer (when hybridized) and upstream of the junction. Typically, the primer is selected such that amplification product synthesized utilizing it and a second primer (located in an *S. aureus* genomic sequence) will be of approximately 200-350 nt in length. While PCR amplification can be designed to generate longer amplicons (e.g., 250, 300, 350, 400, 500, 600, 700, 800, 900, 1000 nt), preferred amplicon lengths for either transcription-based (e.g., NASBA or TMA) or PCR-type reactions will be within about 200-300 nt (e.g. 150, 200, 250, 300 nt) in length. Additionally, for a multiplex amplification reaction, whether transcription-based or PCR-based, an amplicon in the range of 200-300 nt or shorter is preferable, to enhance sensitivity of the test.

As used in the claims, "amplification conditions" are those appropriate for a selected amplification reaction, as are known to those of skill in the art, such as are utilized in various amplification reactions. Such conditions can be optimized for a specific reaction, primers, etc. as also known by the skilled artisan. As is known, such amplification conditions include contact with the required reagents for the amplification, e.g., nucleotides and enzymes, as well as the appropriate selected temperature, salt and pH conditions, among other aspects. Furthermore, as used in the claims, a primer or probe may be a primer or probe set, i.e., multiple primers or probes. Such primer/probe sets can be utilized in a reaction in which more than one type or subtype of MRSA is desired to be amplified and/or detected, and wherein the nucleic acid sequence of the target MRSA region selected for hybridization of the primer and/or probe varies among types and/or subtypes. Individual primers/probes can be designed for each type or subtype, as exemplified herein.

Specific primers useful for amplifying extremity junction regions can readily be designed, given the teachings herein. Primers for hybridizing to SCCmec right extremity region can include the primers set forth in SEQ ID NOs: 1, 2, 3, 4, 5, and 6, as well as primers comprising these sequences and primers consisting essentially of these sequences. Specific primers for hybridizing to orfX can include the primer set forth in SEQ ID NO: 13, as well as a primer comprising this sequence and a primer consisting essentially of this sequence. Probes for hybridizing to SCCmec right extremity region can include the probes set forth in SEQ ID NOs: 7, 8, 9, 10, 11, and 12, as well as probes comprising these sequences and probes consisting essentially of these sequences. Primers for hybridizing to mecA can include the primers set forth in SEQ ID NOs: 15 and 16 as well as primers comprising these sequences and primers consisting essentially of these sequences. Either can readily be adapted as a P1-type or a P2 type (for NASBA-type amplifications). Probes for hybridizing to mecA can include the probe set forth in SEQ ID NO: 14 as well as probes comprising this sequence and probes consisting essentially of this sequence.

The present invention further provides a method of identifying the presence in a sample of a methicillin-resistant *Staphylococcus aureus* (MRSA) having an insertion of an SCCmec cassette within *Staphylococcus aureus* chromosomal DNA which comprises the steps of;

bringing, in a single container, the biological sample in contact with a. a first oligonucleotide set comprising (1) a first oligonucleotide having a nucleic acid sequence that specifically hybridizes to an extremity junction region of a SCCmec cassette, and (2) a second oligonucleotide having a nucleic acid sequence that specifically hybridizes to a *Staphylococcus aureus* chromosomal DNA region flanking said SCCmec cassette to form a first reaction product of the biological sample and the first and second oligonucleotides, and b. a second oligonucleotide set comprising (3) a third oligonucleotide having a nucleotide sequence that specifically hybridizes to a first region of mecA nucleic acid and (4) a fourth oligonucleotide having a nucleotide sequence that specifically hybridizes to a second region of mecA nucleic acid to form a second reaction product of the biological sample and the third and fourth oligonucleotides; and identifying the presence of MRSA by detecting both a first and a second reaction product. The first and second reaction products can be formed by an amplification reaction. Conditions under which the reagents are brought in contact with the sample can be conditions appropriate for a selected amplification reaction. The identifying step can, in one embodiment, comprise contacting the first and second reaction products with (1) a first probe capable of specifically hybridizing with the first reaction product, if present, and (2) a second probe capable of specifically hybridizing with the second reaction product, if present.

As used herein, an oligonucleotide "having" a nucleic acid sequence included in a portion of target DNA means the sequence has sufficient identity to the target DNA sequence, or its complement, to specifically and selectively hybridize to that target DNA under stringent hybridization conditions. It includes nucleic acid sequences having full sequence identity to the sequence. In the single container can be included all components of a reaction mixture, tailored to the specific amplification and detection method utilized. Thus, a "reaction mixture" can include all the necessary reactants for performing a reaction, which may include, but not be limited to, buffering agents to maintain pH at a selected level during a reaction, salts, co-factors, scavengers, and the like.

Generally, amplification reactions producing amplicons (the product of a polynucleotide amplification reaction) are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Amplification can include any known or newly designed method of amplification, including those used in published methods (e.g., transcription-based amplification such as transcription-mediated amplification (TMA) and nucleic acid sequence-based amplification NASBA (as exemplified herein), and cycling nucleic acid amplification technologies (thermocycling) such as polymerase chain reaction (PCR), reverse transcriptase PCR (RT-PCR), and ligase chain reaction (LCR), and any method of amplification, e.g., sustained sequence replication (3SR), strand displacement amplification (SDA), branched DNA (bDNA), cycling probe technology (CPT), solid phase amplification (SPA), rolling circle amplification technology (RCA), solid phase RCA, anchored SDA and nuclease dependent signal amplification (NDSA), all of which are known to the skilled artisan. An amplification reaction may be a "real-time" amplification if a detection chemistry is available that permits a reaction product to be measured as the amplification reaction progresses, e.g. real-time PCR or real-time NASBA. Thus this invention includes the use of any nucleic acid amplification method or any other procedure which may be used to increase the sensitivity and/or the rapidity of nucleic acid-based diagnostic tests. The present invention also includes the use of any detection technology including post-amplification detection technologies, any amplification technology combined with detection, any hybridization nucleic acid chips or array technologies, and any amplification chips or combination of amplification and hybridization chip technologies. Detection and identification by any nucleotide sequencing method is also within the present invention.

While any suitable amplification methods can be utilized for the present assay, it is noted that amplification reactions that utilize a restriction enzyme, such as DNA-NASBA, can contribute an additional level of specificity to the assay. For example, if one selects a DNA-NASBA amplification reaction having a P1 capable of hybridizing in the *S. aureus* orfX region, the requirement that the correct restriction site be present in the genomic region of the *S. aureus* for amplification to occur greatly reduces or eliminates the likelihood of amplification of a methicillin-resistant coagulase-negative *Staphylococcus* (e.g., methicillin-resistant *S. epidermidis*) since it should not have the requisite restriction site. This is particularly useful in "approach 2" reactions of this present invention, wherein the probe to detect the junction between bacterial genomic DNA and SCCmec DNA is designed to hybridize to SCCmec DNA (or primarily to SCCmec DNA, with, in one embodiment, one, two, three or a few probe nucleotides hybridizing across the junction to orfX DNA), rather than to genomic bacterial DNA. The combination of these features provides a highly specific assay for MRSA. Furthermore, additional specificity can be attained with PCR-type reactions by increasing the stringency of hybridization conditions of the primers. Thus, by increasing the stringency of the selected amplification reaction, by any selected means, one can increase the overall specificity of MRSA assays that include detection reactions that utilize an SCCmec-hybridizing probe.

Furthermore, amplification can be conducted in additional manners to enhance amplification, for example, for transcription-based amplification reactions, (e.g., TMA, NASBA), a blocked "P1" (i.e. promoter-bearing) primer can be utilized, if desired. Such blocked primers are typically blocked at their 3' end from extension of the primer, by a chemical moiety, such as dabsyl, others being known in the art.

A variety of detection methods can be utilized in this invention. Detection methods utilizing nucleic acid probes are well known in the art. Probes of the present kits and/or for use in the present methods can be labeled by any selected label suitable for the detection method chosen, many of which are known in the art, such as a phosphatase (e.g., alkaline phosphatase), biotin, avidin, a peroxidase (e.g., horseradish peroxidase), digoxigenin, a fluorescent dye (such as Cy3 and Cy5 dyes, fluorescein, FAM, ROX), a chemiluminescent label, a chromophoric label, a radioactive label (e.g., a radioisotope) and a ligand. Probe designs for different detection methods can be utilized, such as target-capture, HPA, Taq-Man, molecular beacons and sandwich hybridization. Hybridization conditions can be selected in accordance with the type of probe and the type of detection reaction selected.

The present method further provides useful kits for use in such amplification and detection methods. Specifically provided is a kit for detection of methicillin-resistant *Staphylococcus aureus* (MRSA) having an insertion of an SCCmec cassette within *Staphylococcus aureus* chromosomal DNA, the kit comprising a first primer capable of specifically hybridizing in an extremity junction region of the SCCmec cassette, a second primer capable of specifically hybridizing to chromosomal *Staphylococcus aureus* DNA in the region of the extremity junction, and a probe capable of specifically hybridizing fully within a region of the SCCmec cassette between the region with which the first primer is capable of hybridizing and the junction, wherein each of the first primer and the second primer is oriented such that, under amplification conditions, the junction is amplified. In one preferred embodiment, the extremity junction region is the right extremity junction region. In another embodiment, the extremity junction region is the left extremity junction region. In one embodiment, the first and second primers are provided in a single container. In another embodiment, the first and second primers and the probe are provided in a single container. Thus, a kit of the invention can comprise a first container comprising a first primer capable of specifically hybridizing in a right extremity junction region of the SCCmec cassette and a second primer capable of specifically hybridizing in a right extremity junction region of chromosomal *Staphylococcus aureus* DNA and a second container comprising a probe capable of specifically hybridizing fully within a region of the SCCmec cassette between the region with which the first primer is capable of hybridizing and the junction. Additionally, a kit of the present invention can comprise a container comprising a first primer capable of specifically hybridizing in a right extremity junction region of the SCCmec cassette, a second primer capable of specifically hybridizing in a right extremity junction region of chromosomal *Staphylococcus aureus* DNA, and a probe capable of specifically hybridizing fully within a region of the SCCmec cassette between the region with which the first primer is capable of hybridizing and the junction.

The present invention further provides a kit for identifying the presence in a sample of a methicillin-resistant *Staphylococcus aureus* (MRSA) having an insertion of an SCCmec cassette within *Staphylococcus aureus* chromosomal DNA which comprises:
a) first amplification and detection oligonucleotide set comprising
1) a first primer capable of specifically hybridizing in an extremity junction region of the SCCmec cassette,
2) a second primer capable of specifically hybridizing to chromosomal *Staphylococcus aureus* DNA in the region of the extremity junction, and
3) a first probe selected from the group consisting of (a) a first probe capable of specifically hybridizing primarily within a region of the SCCmec cassette between the region with which the first primer is capable of hybridizing and the junction, and (b) a first probe capable of specifically hybridizing fully within a region of the SCCmec cassette between the region with which the first primer is capable of hybridizing and the junction,
wherein each of the first primer and the second primer is oriented such that, under amplification conditions, the junction is amplified, and
b) a second amplification and detection oligonucleotide set comprising
4) a third primer capable of specifically hybridizing to a first region of mecA,
5) a fourth primer capable of specifically hybridizing to a second region of mecA, and
6) a second probe capable of specifically hybridizing to a region of mecA between the first and second regions of mecA,
wherein each of the third primer and the fourth primer is oriented such that, under amplification conditions, the region of mecA between the first and second regions of mecA is amplified.

The present invention additionally provides a kit for identifying the presence in a sample of a methicillin-resistant *Staphylococcus aureus* (MRSA) having an insertion of an SCCmec cassette within *Staphylococcus aureus* chromosomal DNA which comprises:
a) first amplification and detection oligonucleotide set comprising
1) a first primer capable of specifically hybridizing in a right extremity junction region of the SCCmec cassette,
2) a second primer capable of specifically hybridizing to chromosomal *Staphylococcus aureus* DNA in the region of the right extremity junction, and
3) a first probe capable of specifically hybridizing primarily, or fully, within a region of the SCCmec cassette between the region with which the first primer is capable of hybridizing and the junction,
wherein each of the first primer and the second primer is oriented such that, under amplification conditions, the junction is amplified, and
b) a second amplification and detection oligonucleotide set comprising
4) a third primer capable of specifically hybridizing to a first region of mecA,
5) a fourth primer capable of specifically hybridizing to a second region of mecA, and
6) a second probe capable of specifically hybridizing to a region of mecA between the first and second regions of mecA,
wherein each of the third primer and the fourth primer is oriented such that, under amplification conditions, the region of mecA between the first and second regions of mecA is amplified.

A probe capable of specifically hybridizing "fully within" a region of the SCCmec cassette between the region with which the first primer is capable of hybridizing and the junction means a probe that hybridizes only within SCCmec cassette, and does not hybridize across the junction, under selected conditions for specific hybridization. A probe capable of specifically hybridizing "primarily within" SCCmec cassette means a probe that hybridizes within SCCmec cassette and can additionally hybridize across the junction and, therefore, includes at least one, or two or three or a few nucleotides of orfX that abut the junction. If one, two three or a few nucleotides of the probe hybridize to a region of orfX abutting the junction, the probe will, however, be capable of at least 75%, at least 80%, at least 85%, at least 90%, at least 91%, at least 92%, at least 93%, at least 94%, at least 95%, at least 96%, at least 97%, at least 98%, or at least 99% of its nucleotides, preferably contiguous nucleotides, specifically hybridizing to a region of the SCCmec cassette between the region with which the first primer is capable of hybridizing and the junction. A probe hybridizing primarily within a region of the SCCmec cassette can include a probe hybridizing fully within a region of the SCCmec cassette.

Probes of this invention, including those included in such kits, can advantageously be labeled for detection, as known by persons of skill in the art. Labels can appropriately be selected for the specific design and type of amplification reaction to be performed. Primer and probe reagents can be provided in any of several states, including dried, lyophilized, pelleted, spray-dried, or in liquid.

Kits of this invention can include additional elements, such as reagents for a selected amplification method (e.g., amplification enzyme(s), buffer(s), and/or restriction enzyme(s), among others), control(s), reaction container(s), and the like. In a specific embodiment, a first, second, third and fourth primers are provided in a single container. In another embodiment, the first and second amplification and detection oligonucleotide sets are provided in a single container. Thus, such kits can be useful for performing multiplex amplifications.

In one embodiment a kit is provided which comprises a container comprising a first primer capable of specifically hybridizing in an extremity junction region, preferably the right extremity junction region, of the SCCmec cassette; a second primer capable of specifically hybridizing in chromosomal *Staphylococcus aureus* DNA in the region of an extremity junction, specifically the right extremity junction region if the first primer hybridizes in the right extremity junction region; a third primer capable of specifically hybridizing to a first region of mecA; and a fourth primer capable of specifically hybridizing to a second region of mecA. Such a kit can further comprise a container comprising a first probe capable of specifically hybridizing fully within a region of the SCCmec cassette between the region with which the first primer is capable of hybridizing and the junction and a second probe capable of specifically hybridizing to a region of mecA between the first and second regions of mecA. Additionally, in another embodiment of the invention, a kit can be provided which comprises a container comprising a first primer capable of specifically hybridizing in an extremity junction region of the SCCmec cassette, preferably the right extremity junction region; a second primer capable of specifically hybridizing in chromosomal *Staphylococcus aureus* DNA in the region of an extremity junction region, specifically the right extremity junction region if the first primer hybridizes in the right extremity junction region; a third primer capable of specifically hybridizing to a first region of mecA; a fourth primer capable of specifically hybridizing to a second region of mecA; a first probe capable of specifically hybridizing fully within a region of the SCCmec cassette between the region with which the first primer is capable of hybridizing and the junction; and a second probe capable of specifically hybridizing to a region of mecA between the first and second regions of mecA.

A primer capable of specifically hybridizing in a right extremity junction region of the SCCmec cassette can be a nucleic acid comprising a sequence selected from the group consisting of: SEQ ID NO: 1, 2, 3, 4, 5, and 6. Furthermore, such a primer can consist essentially of, or consist of, a sequence selected from the group consisting of: SEQ ID NO: 1, 2, 3, 4, 5, and 6. One or more such primers can be selected; in a preferred embodiment, several primers, each specific for a different type of MRSA, are selected for inclusion in a kit. Such primers are useful in the methods of this invention.

A primer capable of specifically hybridizing in chromosomal *Staphylococcus aureus* DNA in the region of the right extremity junction can preferably be a primer that is capable of specifically hybridizing to orfX. More specifically, in one embodiment, this primer can comprise the nucleic acid set forth as SEQ ID NO: 13. Furthermore, such a primer can consist essentially of, or consist of, the nucleic acid set forth as SEQ ID NO: 13. Such primers are useful in the methods of this invention.

A probe capable of specifically hybridizing fully within a region of the SCCmec cassette between the region with which the first primer is capable of hybridizing and the junction can, in one embodiment, comprise five or more probes, each capable of hybridizing specifically to a different type of MRSA. In a specific embodiment, such a probe can comprise a sequence selected from the group consisting of SEQ ID NOs: 7, 8, 9, 10, 11, and 12. Furthermore, such a probe can consist essentially of, or consist of, a sequence selected from the group consisting of SEQ ID NOs: 7, 8, 9, 10, 11, and 12. Such probes are useful in the methods of this invention.

In certain kits of the invention, primers and/or probes for detection of mecA gene are included. Such a kit can include a primer set specific for the mecA gene, specifically, a first primer capable of specifically hybridizing to a first selected region of mecA wherein the first primer is oriented such that, under amplification conditions, the region of mecA between the first region of mecA and a second selected region of mecA is amplified, and a second primer capable of specifically hybridizing to the second selected region of mecA wherein the second primer is oriented such that, under amplification conditions with the first primer, the region of mecA between the first region of mecA and the second region of mecA is amplified. In one embodiment, these mecA primers can include one or both of SEQ ID NOs: 15 and 16. The kit can further include a probe specific for the region of mecA between the two selected mecA primers. In a specific embodiment, such a mecA probe can comprise the nucleic acid sequence set forth in SEQ ID NO: 14. Furthermore, such a mecA probe can consist essentially of the nucleic acid sequence set forth in SEQ ID NO: 14. By providing primer and probe sets for amplifying and detecting both SCCmec cassette and mecA, within the same kit for use within the same reaction container, a useful multiplex kit for detecting MRSA can be provided.

It is noted that references to primer and probe sequences that include thymidine can be readily adapted to utilize uridine in substitution for thymidine, where useful for the particular assay. Furthermore, nucleotides may be modified by addition of chemical groups, or substitution of individual residues by analogues (e.g., 2'-O-methoxy versions). Additional such modified nucleotides are known in the art; some examples include hydroxymethyl nucleotides, methylated nucleotides, fluorinated nucleotides, alpha thio phosphate nucleotides, amine-modified nucleotides, methoxy nucleotides, carboxymethyl nucleotides, thio nucleotides, inosine, dihydrouridine, psuedouridine, wybutosine, queuosine, C7dGTP. Additional modified nucleotides are found in U.S. Pat. Nos. 5,405,950 and 5,633,364 (both, Mock and Lovern). Furthermore, a probe can comprise DNA, RNA, modified DNA or RNA, PNA, other synthetic nucleic acids or nucleic acid substitutes that use nucleotide bases as means of selectively hybridizing to a target.

Throughout this application, a particular oligonucleotide may be exemplified in use as a particular primer type (e.g. NASBA P1-type (linked to a sequence that provides a promoter region when in double-stranded form) or P2-type (used alone or linked to a tag oligonucleotide) primer); however, such use should not limit the use(s) for which the oligonucleotide may be useful. For example, a primer exemplified as a P1 primer may be useful as a P2-type primer. Additionally, primers can be adapted for other amplification methods (e.g., the T7 polymerase promoter region of P1 (for NASBA or TMA) removed for PCR use), as is known by the skilled artisan.

The nucleic acid sequence of the T7 promoter is well-known to persons skilled in the art, and though a particular sequence is exemplified herein, functional equivalents having slight variations, known in the art or newly designed, may be selected. In a preferred embodiment, the sequence of the T7 promoter is that set forth in SEQ ID NO:17.

The present method can be utilized on any selected sample, such as a direct patient sample, e.g., nasal or inguinal swab, throat swab, rectal swab, samples from wounds, all particularly suitable for screening, as well as particularly suitable for diagnosis, bronchoalveolar lavage or blood (e.g., septicemia or blood culture). Such samples typically contain a mixed population of organisms. Additionally, if desired, this method can be applied to a sample having only a single bacterial species or strain, e.g., samples utilizing isolation, culture, capture, and/or enrichment of MRSA.

The present invention is exemplified in the following examples.

EXAMPLES

A study was initiated using NASBA as amplification. Two main approaches were investigated: approach 1 (generic *S. aureus* (orfX) probes) and approach 2 (SCCmec-specific probes). "Approach 1" is very similar to the configuration used in previous tests; it is based on the use of 5 P2 located in the right part of the cassette, one generic P1 located in *S. aureus* orfX and one generic beacon located in *S. aureus* orfX (FIG. 2). The herein described "approach 2" uses the same five P2 and P1 as approach 1, but five SCCmec-specific beacons located in the right part of the cassette are used instead of the generic beacon (see FIG. 3). Furthermore, is it also described and shown herein that a multiplex reaction utilizing approach 2 with amplification and detection of mecA was found to be highly effective at detecting MRSA.

Amplification Conditions

For all experiments, the following DNA NASBA conditions were used: Chromosomal DNA was used as input material for amplification. For each strain, bacterial suspensions were standardized to 0.5 McFarland ($1.5 \times 10^8$ CFU/ml) using densitometer (bioMerieux, Marcy l'Etoile, France). DNA was released from bacterial cells using a mechanical lysis technique with glass beads and vortex, and finally serial dilutions were prepared from the lysed suspension.

Amplification was performed using standard NASBA reagents (40 mM Tris-HCl pH 8.5, 12 mM $MgCl_2$, 90 mM KCl, 15% v/v DMSO, 5 mM DTT, 1 mM each dNTP, 2 mM ATP, 2 mM CTP, 2 mM UTP, 1.5 mM GTP, 0.5 mM ITP; the concentration of primers (forward primer=P1 and reverse primer=P2) was 0.2 µM when tested in monoplex and 0.1 µM when tested in multiplex; the concentration of FAM labeled molecular beacon probe(s) was 0.01 µM and 0.1 µM for Cy5 labeled beacon probe.

Concentration of restriction enzyme (Sau3A-I) was 0.05 Units per µl in the NASBA reaction. Incubation of the mixture for 15 min at 41° C. enabled the restriction enzyme(s) to cut the DNA, this step was followed by 5 min at 95° C. for DNA denaturation and restriction enzyme(s) degradation, finally a 3 min step at 41° C. was performed before adding NASBA enzymes (0.08 units RNase H, 32 units T7 RNA polymerase, 6.4 units AMV reverse transcriptase and 2.1 µg BSA). The reaction mixture was mixed by gently vortexing and short centrifugation, and the amplification and real-time detection was started. The reaction mixture was incubated at 41° C. in the NucliSens EasyQ Analyzer (NucliSens, BioMérieux) for 90 minutes with fluorescence monitoring every 30 seconds. For FAM detection, the reactions were excited at 485 nm and the emission signal was measured at 518 nm. For ROX, excitation and emission were performed at 578 nm and 604 nm respectively and for Cy5, excitation and emission were performed at 646 am and 678 nm respectively.

Primers and probes utilized are set forth below. For NASBA reactions, "primer 1" or "P1" is traditionally (as here) used to indicate the primer having at its 5' end a sequence that provides a promoter region (here, for T7 polymerase) when in double-stranded form. The second primer for NASBA, a non-promoter-linked primer, is traditionally, as here, labeled "Primer 2" or "P2."

The following Table 1 provides sequences for primers and probes utilized in the Examples.

TABLE 1

| Function | SEQ ID NO | Description | Sequence 5' → 3' |
| --- | --- | --- | --- |
| P2 | 1 | SCCmec Right extremity junction region MREJ type v | CTCTGCTTTATATTATAAAATTACGGCTG |
| P2 | 2 | SCCmec Right extremity junction region MREJ type iii | ATTTCATATATGTAATTCCTCCACATCTC |
| P2 | 3 | SCCmec Right extremity junction region MREJ type i and ii | AAGACTGCGGAGGCTAA |
| P2 | 4 | SCCmec Right extremity junction region MREJ type vii | TATTCTTCAAAGATTTGAGC |
| P2 | 5 | SCCmec Right extremity junction region MREJ type iv | CAAATATTATCTCGTAATTTAC |
| P2 | 6 | SCCmec Right extremity junction region SCCmec type V | TCTAATTTATTTAACATAAAATCAATCCT |
| Beacon-FAM | 7 | SCCmec Right extremity junction region MREJ type i and ii | FAM-CGGCGCGT CAAAAATCATGAACCTC ATTACTTATGCGCCG-DabSyl |

TABLE 1-continued

| Function | SEQ ID NO | Description | Sequence 5' → 3' |
|---|---|---|---|
| Beacon-FAM | 8 | SCCmec Right extremity junction region MREJ type iii | FAM-CGAGCGC AAATTATACACAACCTAA TTTTTAGTGCGCTCG-DabSyl |
| Beacon-FAM | 9 | SCCmec Right extremity junction region MREJ type vii | FAM-CGGAGCTAATTTAATAATTTTCTCAT ATTTTTTAGCTCCG-Dabsyl |
| Beacon-FAM | 10 | SCCmec Right extremity junction region MREJ type iv | FAM-CGTAACG GATAAAAAACCGCATCATTTGA CGTTACG-Dabsyl |
| Beacon-FAM | 11 | SCCmec Right extremity junction region MREJ type v | FAM-CGTAGCG GCTGAAATAACCGCATCATTTA CGCTACG-Dabsyl |
| Beacon-FAM | 12 | SCCmec Right extremity junction region SCCmec type V | FAM-CGTCACGTAAAATATATTATACAC AATCCGTTTCGTGACG-Dabsyl |
| P1 | 13 | OrfX Right extremity junction region | aattctaatacgactcactatagggagag TCAAACGGCCTGCACAAGGA |
| Beacon-Cy5 | 14 | mecA gene | Cy5-CGTACGGGATCATAGCGTCATTATT CGTACG-Dabsyl |
| P1 | 15 | mecA P1 | aattctaatacgactcactatagggagag GTATTGGCCAATTCCACATTGTTTC |
| P2 | 16 | mecA P2 | CATTGATCGCAACGTTCA |
| T7 polymerase promoter sequence | 17 | | AATTCTAATACGACTCACTATAGGG |
| Beacon-FAM | 18 | Generic-orfX (SCCmec) | FAM-CGTACGGTAGTTACTGCGTTGTAAGACGT ACG-Dabsyl |

Example 1

NASBA Results Obtained with Approach 1 (Generic Beacon NASBA) on 21 MSSA Strains "Approach 1" is based on the use of 5 P2 located in the right part of the cassette, one generic P1 located in *S. aureus* orfX and one generic beacon located in *S. aureus* orfX (FIG. 2). A DNA NASBA was performed using five SCCmec cassette-specific Primers 2 (P2) (SEQ ID NO: 1, SEQ ID NO: 2, SEQ ID NO: 3, SEQ ID NO: 4, SEQ ID NO: 5), one generic P1 (SEQ ID NO: 13) and one generic FAM-labeled beacon (SEQ ID NO: 18) NASBA curves were obtained for MRSA (6 strains belonging to MREJ types i, ii, iii, iv, v and vii) and MSSA. Lysate input corresponds to $10^5$ CFU per NASBA. Max signal ratio (ratio between final signal and initial background) are given in Table 2. This experiment shows positive max signal ratio for 5 out of 21 MSSA strains (24%) with the generic beacon NASBA (approach 1).

TABLE 2 max signal ratio obtained for MSSA with generic beacon NASBA (positive signals are in bold italics)

| strain | Max signal ratio |
|---|---|
| MSSA 10 | 1.01 |
| MSSA 11 | *1.69* |

TABLE 2-continued max signal ratio obtained for MSSA with generic beacon NASBA (positive signals are in bold italics)

| strain | Max signal ratio |
|---|---|
| MSSA 12 | 1.02 |
| MSSA 13 | 1.07 |
| MSSA 14 | 1.08 |
| MSSA 15 | 1.00 |
| MSSA 16 | *2.06* |
| MSSA 17 | *2.38* |
| MSSA 18 | *1.52* |
| MSSA 19 | 1.00 |
| MSSA 23 | 1.02 |
| MSSA 24 | 1.00 |
| MSSA 25 | 1.00 |
| MSSA 26 | 1.00 |
| MSSA 27 | *1.38* |
| MSSA 28 | 1.00 |
| MSSA 29 | 1.00 |
| MSSA 30 | 1.00 |
| MSSA 31 | 1.05 |
| MSSA 32 | 1.00 |
| MSSA 1034 | 1.00 |

Example 2

NASBA Results Obtained with Approach 2 (Specific Beacons NASBA) on 6 MRSA Strains and 18 MSSA Strains To overcome non specific detection of MSSA, "approach 2" was defined and developed. Specifically, beacons located in the right part of the SCCmec cassette instead of in the orfX were defined. "Approach 2" uses five specific Primers 2 (P2) and one generic P1, but five specific beacons located in the right part of the cassette are used instead of a generic beacon (see FIG. 3).

A DNA NASBA was performed using five SCCmec cassette-specific primers 2 (P2) (SEQ ID NOs: 1-5), one generic (orfX) primer 1 (P1) (SEQ ID NO: 13) and five SCCmec cassette-specific FAM-labeled beacons (SEQ ID NO: 7, SEQ ID NO: 8, SEQ ID NO: 9, SEQ ID NO: 10, SEQ ID NO: 11). Six MRSA and 18 MSSA strains were tested using a lysate as target corresponding to $10^5$ CPU per NASBA. NASBA curves were obtained on MRSA and MSSA. Max signal ratio obtained are given in Table 3.

This experiment shows that only one out of 18 MSSA was detected with specific beacons approach (approach 2); this detected MSSA strain is expected to possess the right part of the cassette without the mecA gene. This experiment shows that the use of specific beacons (approach 2) significantly reduces the percentage of MSSA that are non specifically detected with the generic beacon approach (approach 1).

TABLE 3 max signal ratio obtained for MSSA and MRSA with specific beacons NASBA (positive signals are in bold italics)

| Strain | mecA PCR | Max signal ratio |
|---|---|---|
| neg control | Not applicable | 1.0 |
| MSSA 10 | neg | 1.0 |
| MSSA 11 | neg | 1.0 |
| MSSA 12 | neg | 1.0 |
| MSSA 13 | neg | 1.0 |
| MSSA 14 | neg | 1.0 |
| MSSA 15 | neg | 1.0 |
| MSSA 16 | neg | *1.7* |
| MSSA 17 | neg | 1.0 |
| MSSA 18 | neg | 1.0 |
| MSSA 19 | neg | 1.0 |
| MSSA 23 | neg | 1.0 |
| MSSA 24 | neg | 1.0 |
| MSSA 25 | neg | 1.0 |
| MSSA 26 | neg | 1.0 |
| MSSA 27 | neg | 1.0 |
| MSSA 28 | neg | 1.0 |
| MSSA 29 | neg | 1.0 |
| MSSA 30 | neg | 1.0 |
| MRSA 3 | pos | *1.6* |
| MRSA 7 | pos | *1.6* |
| MRSA 8 | pos | *1.7* |
| MRSA 9 | pos | *2.2* |
| MRSA 10 | pos | *2.1* |
| MRSA 11 | pos | *1.9* |

Example 3

Multiplex Amplification and Detection of mecA Gene and Cassette Insertion Region Using approach 2, some false positives are eliminated, thus providing an improved method for detecting MRSA. However, MSSA strains possessing the cassette without the mecA gene can be detected, and a further improvement was investigated. As shown in this example, simultaneous amplification and detection of both the insertion cassette region, using approach 2, and the mecA gene (see FIG. 4) can help reduce detection of such strains (false MRSA positive).

This example shows the feasibility of a multiplex NASBA for detection of both the mecA gene and the cassette junction region (approach 2, which has SCCmec cassette-specific beacons) in the same tube. This NASBA makes use of 5 SCCmec cassette-specific P2 (SEQ ID NOs: 1-5), 1 P1 (SEQ ID NO: 13) and 5 FAM-labeled SCCmec cassette-beacons (SEQ ID NOs: 7-11) for the cassette junction region and 1 P1 (SEQ ID NO: 15), 1 P2 (SEQ ID NO: 16) and 1 ROX-labeled beacon (SEQ ID NO: 14) for mecA. A NASBA reaction targeting only the SCCmec right extremity junction region, amplified in one tube (five SCCmec cassette-specific P2 (SEQ ID NOs: 1-5), five specific SCCmec cassette-specific FAM beacons (SEQ ID NOs: 7-11) and one orfX P1 (SEQ ID NO: 13)), is also performed for comparison.

The following table (Table 4) gives max signal ratios obtained for (1) SCCmec right extremity junction NASBA (FAM signal) when only the SCCmec right extremity junction region is amplified in one tube (five P2, five specific FAM beacons and one P1 ("SCCmec junction only") and (2) SCCmec right extremity junction NASBA (FAM signal) and mecA NASBA (ROX signal) when both NASBA were performed in the same tube ("SCCmec junction and mecA NASBA in one tube") (max signal ratio are considered positive when >1.2).

TABLE 4

| | type i | type ii | | type iii | |
|---|---|---|---|---|---|
| | | SCCmec | | | |
| | SCCmec junction only | SCCmec junction and mecA NASBA in one tube | SCCmec junction only | SCCmec junction and mecA NASBA in one tube | SCCmec junction only | SCCmec junction and mecA NASBA in one tube |
| CFU/NASBA | FAM | FAM | ROX | FAM | FAM | ROX | FAM | FAM | ROX |
| 1000 | *1.90* | *1.84* | *4.75* | *2.02* | *2.07* | *4.86* | *1.50* | *1.39* | *4.73* |
| 100 | *1.85* | *1.84* | *4.75* | *2.03* | *1.97* | *4.74* | *1.48* | *1.39* | *4.53* |
| 10 | *1.87* | *1.84* | *4.72* | *1.88* | *1.88* | *4.63* | *1.49* | *1.36* | *4.60* |
| 5 | *1.85* | *1.85* | *4.80* | 1.01 | *1.69* | *4.58* | 1.01 | *1.40* | *4.41* |

TABLE 4-continued

| | type iv | | | type v | | | type vii | | |
| | | | | SCCmec | | | | | |
| | SCCmec | SCCmec junction and mecA NASBA in one tube | | SCCmec junction only | junction and mecA NASBA in one tube | | SCCmec junction only | SCCmec junction and mecA NASBA in one tupe | |
| CFU/NASBA | FAM | FAM | ROX | FAM | FAM | ROX | FAM | FAM | ROX |
|---|---|---|---|---|---|---|---|---|---|
| 1000 | *1.62* | *1.64* | *4.85* | *1.14* | *1.39* | *4.81* | *2.41* | *2.43* | *4.83* |
| 100 | *1.57* | *1.48* | *4.58* | *1.42* | *1.33* | *4.69* | *2.44* | *2.43* | *4.81* |
| 10 | *1.61* | *1.50* | *4.62* | *1.43* | 1.00 | *4.03* | *2.40* | 1.00 | *4.59* |
| 5 | *1.61* | *1.44* | *4.15* | *1.43* | 1.01 | 1.00 | *2.40* | 1.01 | 1.01 |

Numbers in bold italics in Table 4 indicate positive signals.

These results show that when SCCmec right extremity junction and mecA NASBA are performed in the same tube, the limit of detection is as low as 5 CFU/NASBA for both SCCmec right extremity junction region and mecA gene with all strain types except types v and vii. Thus, in the case of an MSSA possessing the insertion cassette region without the mecA gene, the present test will properly provide a "MRSA negative" result (SCCmec junction (+) plus mecA (−)).

Example 4

Multiplex Amplification and Detection of mecA Gene and Cassette Insertion Region A multiplex (same reaction tube) amplification and detection of MRSA was performed, utilizing approach 2 (SCCmec cassette-specific beacons) along with mecA detection (same conditions as described in Example 3), utilizing six SCCmec cassette-specific P2 (SEQ ID NOs: 1-6), six specific SCCmec cassette-specific FAM beacons (SEQ ID NOs: 7-12) and one orfX P1 (SEQ ID NO: 13). Positive detection of the MRSA strains was obtained.

Publications cited herein and the material for which they are cited are specifically incorporated by reference. Nothing herein is to be construed as an admission that the invention is not entitled to antedate such disclosure by virtue of prior invention.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting in a sample a methicillin-resistant *Staphylococcus aureus* (MRSA) having an insertion of an SCCmec cassette within *Staphylococcus aureus* chromosomal DNA, the method comprising
   (a) performing on the sample an amplification and detection reaction that detects the presence of a junction of an inserted SCCmec cassette and *Staphylococcus aureus* chromosomal DNA, and
   (b) performing on the sample an amplification and detection reaction that detects the presence of mecA gene,
   wherein if the sample contains MRSA, the presence of both the junction and mecA in the sample is detected.

2. The method of claim 1, wherein the amplification of the junction is performed utilizing
   1) a first primer capable of specifically hybridizing in an extremity junction region of the SCCmec cassette,
   2) a second primer capable of specifically hybridizing in an extremity junction region of chromosomal *Staphylococcus aureus* DNA, and
   3) a first probe capable of specifically hybridizing to a region of the SCCmec cassette between the region with which the first primer is capable of specifically hybridizing and the junction,
   wherein each of the first primer and the second primer is oriented such that, under amplification conditions, the junction is amplified.

3. The method of claim 2, wherein the first primer comprises more than one primer capable of hybridizing in an extremity junction region of the SCCmec cassette.

4. The method of claim 2, wherein the first probe comprises more than one probe, each capable of hybridizing specifically to a different type of MRSA.

5. The method of claim 2, wherein the first probe comprises five or more probes, each capable of hybridizing specifically to a different type of MRSA.

6. The method of claim 1, wherein the extremity junction region is the right extremity junction region.

7. A kit for detection of methicillin-resistant *Staphylococcus aureus* (MRSA) having an insertion of an SCCmec cassette within *Staphylococcus aureus* chromosomal DNA, comprising
   (a) a first primer capable of specifically hybridizing in an extremity junction region of the SCCmec cassette,
   (b) a second primer capable of specifically hybridizing to chromosomal *Staphylococcus aureus* DNA in the region of the extremity junction, and
   (c) a probe selected from the group consisting of (1) a first probe capable of specifically hybridizing primarily within a region of the SCCmec cassette between the region with which the first primer is capable of hybridizing and the junction, and (2) a first probe capable of specifically hybridizing fully within a region of the SCCmec cassette between the region with which the first primer is capable of hybridizing and the junction,
   wherein the probe comprises a detectable label which is a phosphatase, biotin, avidin, peroxidase, digoxigenin, fluorescent dye, chemiluminescent label, radioactive label, or ligand, and
   wherein each of the first primer and the second primer is oriented such that, under amplification conditions, the junction is amplified.

8. The kit of claim 7, further comprising
   d) a third primer capable of specifically hybridizing to a first region of mecA,
   e) a fourth primer capable of specifically hybridizing to a second region of mecA, and
   f) a second probe capable of specifically hybridizing to a region of mecA between the first and second regions of mecA,
   wherein each of the third primer and the fourth primer is oriented such that, under amplification conditions, the region of mecA between the first and second regions of mecA is amplified.

9. The kit of claim 8, wherein the first, second, third and fourth primers are provided in a single container.

10. The kit of claim 7, wherein the first primer is a nucleic acid comprising a sequence selected from the group consisting of: SEQ ID NO: 1, 2, 3, 4, 5, and 6.

11. The kit of claim 7, wherein the second primer is capable of specifically hybridizing to orfX.

12. The kit of claim 7, wherein the second primer comprises the nucleic acid set forth as SEQ ID NO: 13.

13. The kit of claim 7, wherein the probe comprises more than one probe, each capable of hybridizing specifically to a different type of MRSA.

14. The kit of claim 7, wherein the probe is a nucleic acid comprising a sequence selected from the group consisting of SEQ ID NO: 7, 8, 9, 10, 11, and 12.

15. A kit for identifying the presence in a sample of a methicillin-resistant *Staphylococcus aureus* (MRSA) having an insertion of an SCCmec cassette within *Staphylococcus aureus* chromosomal DNA which comprises:
   a) first amplification and detection oligonucleotide set comprising
      1) a first primer capable of specifically hybridizing in a right extremity junction region of the SCCmec cassette,
      2) a second primer capable of specifically hybridizing in chromosomal *Staphylococcus aureus* DNA in the region of the extremity junction, and
      3) a first probe capable of specifically hybridizing within a region between the region with which the first primer is capable of hybridizing and the region with which the second primer is capable of hybridizing, wherein each of the first primer and the second primer is oriented such that, under amplification conditions, the junction is amplified, and b) a second amplification and detection oligonucleotide set comprising 4) a third primer capable of specifically hybridizing to a first region of mecA,
5) a fourth primer capable of specifically hybridizing to a second region of mecA, and
6) a second probe capable of specifically hybridizing to a region of mecA between the first and second regions of mecA, wherein each of the third primer and the fourth primer is oriented such that, under amplification conditions, the region of mecA between the first and second regions of mecA is amplified, and wherein at least one of the first probe and the second probe comprises a detectable label which is a phosphatase, biotin, avidin, peroxidase, digoxigenin, fluorescent dye, chemiluminescent label, radioactive label, or ligand.

16. The kit of claim 15, wherein the first, second, third and fourth primers are provided in a single container.

17. The kit of claim 15, wherein the third primer comprises a nucleic acid selected from the group consisting of SEQ ID NO: 15 and 16.

18. The kit of claim 15, wherein the fourth primer comprises a nucleic acid selected from the group consisting of SEQ ID NO: 15 and 16.

19. The kit of claim 15, wherein the second probe comprises the nucleic acid set forth in SEQ ID NO: 14.

20. An oligonucleotide composition comprising:

(1) a first oligonucleotide having a nucleic acid sequence that specifically hybridizes to an extremity junction region of a SCCmec cassette;
(2) a second oligonucleotide having a nucleic acid sequence that specifically hybridizes to a *Staphylococcus aureus* chromosomal DNA region flanking said SCCmec cassette;
(3) a first probe capable of specifically hybridizing to a region between the region with which the first primer is capable of hybridizing and the region with which the second primer is capable of hybridizing;
(4) a third oligonucleotide having a nucleotide sequence that specifically hybridizes to a first region of mecA nucleic acid;
(5) a fourth oligonucleotide having a nucleotide sequence that specifically hybridizes to a second region of mecA nucleic acid; and
(6) a second probe capable of specifically hybridizing to a region of mecA between the first and second regions of mecA, wherein at least one of the first probe and the second probe comprises a detectable label which is a phosphatase, biotin, avidin, peroxidase, digoxigenin, fluorescent dye, chemiluminescent label, radioactive label, or ligand.

* * * * *

UNITED STATES PATENT AND TRADEMARK OFFICE
CERTIFICATE OF CORRECTION

PATENT NO. : 9,273,360 B2  
APPLICATION NO. : 13/729529  
DATED : March 1, 2016  
INVENTOR(S) : Jay et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this  
Second Day of August, 2016

Michelle K. Lee  
*Director of the United States Patent and Trademark Office*

SEQUENCE LISTING

```
<160> NUMBER OF SEQ ID NOS: 18

<210> SEQ ID NO 1
<211> LENGTH: 29
<212> TYPE: DNA
<213> ORGANISM: Artificial
<220> FEATURE:
<223> OTHER INFORMATION: NABSA primer

<400> SEQUENCE: 1
ctctgcttta tattataaaa ttacggctg                                     29

<210> SEQ ID NO 2
<211> LENGTH: 29
<212> TYPE: DNA
<213> ORGANISM: Artificial
<220> FEATURE:
<223> OTHER INFORMATION: NABSA primer

<400> SEQUENCE: 2
atttcatata tgtaattcct ccacatctc                                     29

<210> SEQ ID NO 3
<211> LENGTH: 17
<212> TYPE: DNA
<213> ORGANISM: Artificial
```

<220> FEATURE:
<223> OTHER INFORMATION: NABSA primer

<400> SEQUENCE: 3
aagactgcgg aggctaa                                                  17

<210> SEQ ID NO 4
<211> LENGTH: 20
<212> TYPE: DNA
<213> ORGANISM: Artificial
<220> FEATURE:
<223> OTHER INFORMATION: NABSA primer

<400> SEQUENCE: 4
tattcttcaa agatttgagc                                               20

<210> SEQ ID NO 5
<211> LENGTH: 22
<212> TYPE: DNA
<213> ORGANISM: Artificial
<220> FEATURE:
<223> OTHER INFORMATION: NABSA primer

<400> SEQUENCE: 5
caaatattat ctcgtaattt ac                                            22

<210> SEQ ID NO 6
<211> LENGTH: 29
<212> TYPE: DNA
<213> ORGANISM: Artificial
<220> FEATURE:
<223> OTHER INFORMATION: NABSA primer

<400> SEQUENCE: 6 tctaattat ttaacataaa atcaatcct                                      29

<210> SEQ ID NO 7
<211> LENGTH: 40
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (40)..(40)
<223> OTHER INFORMATION: 5' Dabsyl modification

<400> SEQUENCE: 7
cggcgcgtca aaaatcatga acctcattac ttatgcgccg                         40

<210> SEQ ID NO 8
<211> LENGTH: 40
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (40)..(40)
<223> OTHER INFORMATION: 5' Dabsyl modification -continued

<400> SEQUENCE: 8
cgagcgcaaa ttatacacaa cctaatttt agtgcgctcg                           40

<210> SEQ ID NO 9
<211> LENGTH: 40
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (40)..(40)
<223> OTHER INFORMATION: 5' Dabsyl modification

<400> SEQUENCE: 9
cggagctaat ttaataattt tctcatattt tttagctccg                           40

<210> SEQ ID NO 10
<211> LENGTH: 36
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (36)..(36)
<223> OTHER INFORMATION: 5' Dabsyl modification

<400> SEQUENCE: 10
cgtaacggat aaaaaaccgc atcatttgac gttacg                              36

<210> SEQ ID NO 11
<211> LENGTH: 36
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (36)..(36)
<223> OTHER INFORMATION: 5' Dabsyl modification

<400> SEQUENCE: 11
cgtagcggct gaaataaccg catcatttac gctacg                              36

<210> SEQ ID NO 12
<211> LENGTH: 40
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (40)..(40)
<223> OTHER INFORMATION: 5' Dabsyl modification

```
<400> SEQUENCE: 12
cgtcacgtaa aatatattat acacaatccg tttcgtgacg                              40

<210> SEQ ID NO 13
<211> LENGTH: 49
<212> TYPE: DNA
<213> ORGANISM: Artificial
<220> FEATURE:
<223> OTHER INFORMATION: NABSA primer

<400> SEQUENCE: 13
aattctaata cgactcacta tagggagagt caaacggcct gcacaagga                    49

<210> SEQ ID NO 14
<211> LENGTH: 31
<212> TYPE: DNA
<213> ORGANISM: Artificial
<220> FEATURE:
<223> OTHER INFORMATION: Oligonucleotide probe sequence
<220> FEATURE:
<221> NAME/KEY: misc_feature
<222> LOCATION: (1)..(1)
<223> OTHER INFORMATION: 3' Cy5 modification
<220> FEATURE:
<221> NAME/KEY: misc_feature
<222> LOCATION: (31)..(31)
<223> OTHER INFORMATION: 5' Dabsyl modification

<400> SEQUENCE: 14
cgtacggrat catagcgtca ttattcgtac g                                       31

<210> SEQ ID NO 15
<211> LENGTH: 54
<212> TYPE: DNA
<213> ORGANISM: Artificial
<220> FEATURE:
<223> OTHER INFORMATION: NABSA promer

<400> SEQUENCE: 15
aattctaata cgactcacta tagggagagg tattggccaa ttccacattg tttc              54

<210> SEQ ID NO 16
<211> LENGTH: 18
<212> TYPE: DNA
<213> ORGANISM: Artificial
<220> FEATURE:
<223> OTHER INFORMATION: NABSA primer

<400> SEQUENCE: 16
cattgatcgc aacgttca                                                      18

<210> SEQ ID NO 17
<211> LENGTH: 25
<212> TYPE: DNA
<213> ORGANISM: Bacteriophage T7

<400> SEQUENCE: 17
aattctaata cgactcacta taggg                                              25

<210> SEQ ID NO 18
<211> LENGTH: 32
<212> TYPE: DNA
<213> ORGANISM: Artificial
<220> FEATURE:
<223> OTHER INFORMATION: Oligonucleotide probe sequence
<220> FEATURE:
```

```
<221> NAME/KEY: misc_feature
<222> LOCATION: (1)..(1)
<223> OTHER INFORMATION: 3' FAM modification
<220> FEATURE:
<221> NAME/KEY: misc_feature
<222> LOCATION: (32)..(32)
<223> OTHER INFORMATION: 5' Dabsyl modification

<400> SEQUENCE: 18
cgtacggtag ttactgcgtt gtaagacgta cg                                    32
```